(12) United States Patent
Sarvazyan

(10) Patent No.: US 11,596,715 B2
(45) Date of Patent: *Mar. 7, 2023

(54) MYOCYTE-DERIVED FLOW ASSIST DEVICE: EXTRAVASAL SHEATHS OF RHYTHMICALLY CONTRACTING MYOCYTES AIDING FLOW OF BIOLOGICAL FLUIDS

(71) Applicant: The George Washington University a Congressionally Chartered Not-for-Profit Corporation, Washington, DC (US)

(72) Inventor: Narine Sarvazyan, Potomac, MD (US)

(73) Assignee: The George Washington University a Congressionally Chartered Not-for-Profit Corporation, Washington, DC (US)

( * ) Notice: Subject to any disclaimer, the term of this patent is extended or adjusted under 35 U.S.C. 154(b) by 904 days.

This patent is subject to a terminal disclaimer.

(21) Appl. No.: 16/511,680

(22) Filed: Jul. 15, 2019

(65) Prior Publication Data
US 2020/0009296 A1  Jan. 9, 2020

Related U.S. Application Data

(63) Continuation of application No. 14/889,830, filed as application No. PCT/US2014/038476 on May 16, 2014, now Pat. No. 10,383,979.
(Continued)

(51) Int. Cl.
*A61L 27/00* (2006.01)
*A61L 27/38* (2006.01)
(Continued)

(52) U.S. Cl.
CPC ............ *A61L 27/3826* (2013.01); *A61F 2/06* (2013.01); *A61K 35/34* (2013.01); *A61L 27/3873* (2013.01); *C12N 5/0657* (2013.01); *C12N 5/0661* (2013.01); *A61F 2002/068* (2013.01); *A61F 2210/0057* (2013.01); *A61F 2210/0066* (2013.01); *A61F 2230/0017* (2013.01); *A61F 2230/0069* (2013.01);
(Continued)

(58) Field of Classification Search
CPC ............ A61L 27/3826; A61L 27/3873; A61L 2430/20; A61F 2/06; A61F 2002/068; A61F 2230/0069; A61F 2230/0091; A61K 35/34; C12N 5/0657; C12N 5/0661
See application file for complete search history.

(56) References Cited

U.S. PATENT DOCUMENTS 4,666,443 A   5/1987  Portner
4,759,760 A   7/1988  Snapp, Jr.
(Continued)

OTHER PUBLICATIONS

International Search Report of PCT/US2014/038476.
(Continued)

*Primary Examiner* — Suzette J Gherbi
(74) *Attorney, Agent, or Firm* — Kory D. Christensen

(57) ABSTRACT

This invention relates, e.g., to a Myocyte-based Flow Assist Device (MFAD) for treating a subject in need of increased flow of a biological fluid, such as venous blood or lymph, comprising a sheath which comprises rhythmically contracting myocytes.

15 Claims, 12 Drawing Sheets

Related U.S. Application Data

(60) Provisional application No. 61/905,491, filed on Nov. 18, 2013, provisional application No. 61/824,180, filed on May 16, 2013.

(51) Int. Cl.
```
A61K 35/34      (2015.01)
A61F 2/06       (2013.01)
C12N 5/077      (2010.01)
```

(52) U.S. Cl.
CPC ... *A61F 2230/0091* (2013.01); *A61L 2430/20* (2013.01); *C12N 2533/00* (2013.01)

(56) References Cited

U.S. PATENT DOCUMENTS

| | | | |
|---|---|---|---|
| 4,813,952 A | | 3/1989 | Khalafalla |
| 5,007,927 A | | 4/1991 | Badylak et al. |
| 6,592,623 B1 | * | 7/2003 | Bowlin ............... A61L 27/34 623/13.17 |
| 7,374,774 B2 | * | 5/2008 | Bowlin ............... C12N 5/0068 424/443 |
| 10,117,759 B2 | * | 11/2018 | Jordan ............... A61L 31/14 |
| 10,173,038 B2 | * | 1/2019 | Campbell ........... A61L 29/085 |
| 10,383,979 B2 | * | 8/2019 | Sarvazyan ......... A61L 27/3826 |
| 10,898,620 B2 | * | 1/2021 | Ramzipoor ......... A61L 31/14 |
| 2004/0009600 A1 | * | 1/2004 | Bowlin ............... A61L 27/24 435/395 |
| 2005/0009178 A1 | * | 1/2005 | Yost ................... C12M 21/08 435/399 |
| 2005/0209687 A1 | * | 9/2005 | Sitzmann ........... C12M 25/14 623/1.41 |
| 2010/0184183 A1 | | 7/2010 | Schussler et al. |
| 2013/0245747 A1 | * | 9/2013 | Jordan ............... A61F 2/2415 623/1.18 |
| 2013/0330378 A1 | | 12/2013 | Parker et al. |
| 2020/0009296 A1 | * | 1/2020 | Sarvazyan .......... C12N 5/0657 |

OTHER PUBLICATIONS

Ahmed et al., "Nanostructured materials for cardiovascular tissue engineering," J. Nanosci. Nanotechnol. 12, 4775-4785 (2012).
Ahmed et al., "Fibrin: a versatile scaffold for tissue engineering applications," Tissue Eng. Part B Rev. 14, 199-215 (2008).
Bakunts et al., "Formation of cardiac fibers in Matrigel matrix," Biotechniques 44, 341-348 (2008).
Beebe-Dimmer et al., "The epidemiology of chronic venous insufficiency and varicose veins," Ann. Epidemiol. 15, 175-184 (2005).
Bian et al., "Local tissue geometry determines contractile force generation of engineered muscle networks," Tissue Eng. Part A 18, 957-967 (2012).
Brorson et al., "Controlled compression and liposuction treatment for lower extremity lymphedema," Lymphology 41, 52-63 (2008).
Carletti et al., "Scaffolds for tissue engineering and 3D cell culture," Methods Mol. Biol. 695, 17-39 (2011).
Casley-Smith, "Alterations of untreated lymphedema and it's grades over time," Lymphology 28, 174-185 (1995).
Cheung et al., "Directed differentiation of embryonic origin-specific vascular smooth muscle subtypes from human pluripotent stem cells," Nat. Protoc. 9, 929-938 (2014).
Chow et al., "Epigenetic regulation of the electrophysiological phenotype of human embryonic stem cell-derived ventricular cardiomyocytes: insights for driven maturation and hypertrophic growth," Stem Cells Dev. 22, 2678-2690 (2013).
Dai et al., "Implantation of immature neonatal cardiac cells into the wall of the aorta in rats: a novel model for studying morphological and functional development of heart cells in an extracardiac environment," Circulation 110, 324-329 (2004).
Dai et al., "Cardiac cells implanted within the outer aortic wall of rats generate measurable contractile force," Regen. Med. 1, 119-124 (2006).
Dai et al., "Development of a spontaneously beating vein by cardiomyocyte transplantation in the wall of the inferior vena cava in a rat: A pilot study," J. Vasc. Surg. 45, 817-820 (2007).
Didem et al., "The comparison of two different physiotherapy methods in treatment of lymphedema after breast surgery," Breast Cancer Res. Treat. 93, 49-54 (2005).
Dongaonkar et al., "Blood flow augmentation by intrinsic venular contraction in vivo," Am. J. Physiol. Regul. Integr. Comp. Physiol. 302, R1436-42 (2012).
Eschenhagen et al., "Engineering myocardial tissue," Circ. Res. 97, 1220-1231 (2005).
Eschenhagen et al., "Cardiac tissue engineering," Transpl. Immunol. 9, 315-321 (2002).
Gärtner et al., "Prevalence of and factors associated with persistent pain following breast cancer surgery," JAMA 302, 1985-1992 (2009).
Greer et al., "Advanced Wound Care Therapies for Non-Healing Diabetic, Venous, and Arterial Ulcers: A Systematic Review," Evidence-based Program, 182 pages, (Nov. 2012).
Hargens et al., "Contractile stimuli in collecting lymph vessels," Am J Physiol Hear. Circ Physiol 233, H57-65 (1977).
Hosoyama et al., "Derivation of myogenic progenitors directly from human pluripotent stem cells using a sphere-based culture," Stem Cells Transl. Med. 3, 564-574 (2014).
Huang et al., "Effects of manual lymphatic drainage on breast cancer-related lymphedema: a systematic review and meta-analysis of randomized controlled trials," World J. Surg. Oncol. 11, 15 (2013).
Joh et al., "External banding valvuloplasty for incompetence of the great saphenous vein: 10-year results," Int. J. Angiol. 18, 25-28 (2009).
Karabekian et al., "Immunological Barriers to Stem-Cell Based Cardiac Repair," Stem Cell Rev. 7, 315-325 (2011).
Keast et al., "Chronic oedema/lymphoedema: under-recognised and under-treated," Int. Wound J., pp. 328-333 (2014).
Khademhosseini et al., "Microfluidic patterning for fabrication of contractile cardiac organoids," Biomed. Microdevices 9, 149-157 (2007).
Laflamme et al., "Formation of Human Myocardium in the Rat Heart from Human Embryonic Stem Cells," Am. J. Pathol. 167, 663-671 (2005).
Lundy et al., "Structural and Functional Maturation of Cardiomyocytes Derived From Human Pluripotent Stem Cells," Stem Cells and Development 22;14 (2013).
Lurie et al., "Invasive treatment of deep venous disease. A UIP consensus," Int. Angiol. 29, 199-204 (2010).
Madden et al., "Proangiogenic scaffolds as functional templates for cardiac tissue engineering," Proc. Natl. Acad. Sci. U. S. A. 107, 15211-15216 (2010).
Maleti et al., "Reconstructive surgery for deep vein reflux in the lower limbs: techniques, results and indications," Eur. J. Vasc. Endovasc. Surg. 41, 837-848 (2011).
Martin et al., "Manual lymphatic drainage therapy in patients with breast cancer related lymphoedema," BMC Cancer 11, 94 (2011).
Meissner et al., "The hemodynamics and diagnosis of venous disease," J. Vasc. Surg. 46 Suppl S, 4S-24S (2007).
Nakatsu et al., "Influence of mesenchymal stem cells on stomach tissue engineering using small intestinal submucosa," J. Tissue Eng. Regen. Med (2013).
Nunes et al., "Biowire: a platform for maturation of human pluripotent stem cell-derived cardiomyocytes," Nat. Methods 10, 781-787 (2013).
Opie et al., "Monocusp—novel common femoral vein monocusp surgery uncorrectable chronic venous insufficiency with aplastic/dysplastic valves," Phlebology 23, 158-171 (2008).
Pavcnik et al., "Percutaneous autologous venous valve transplantation: short-term feasibility study in an ovine model," J. Vasc. Surg. 46, 338-345 (2007).
Petrek et al., "Lymphedema in a cohort of breast carcinoma survivors 20 years after diagnosis," Cancer 92, 1368-1377 (2001).
Phillips et al., "Endovenous valve transfer for chronic deep venous insufficiency," Eur. J. Vasc. Endovasc. Surg. 46, 360-365 (2013).

(56) References Cited

OTHER PUBLICATIONS

Riolobos et al., "HLA engineering of human pluripotent stem cells," Mol. Ther. 21, 1232-1241 (2013).

Robertson et al., "Epidemiology of chronic venous disease," Phlebology 23, 103-111 (2008).

Sakaguchi et al., "In vitro engineering of vascularized tissue surrogates," Sci. Rep. 3, 1316 (2013).

Sarvazyan, "Thinking outside the heart: Use of engineered cardiac tissue for treatment of chronic deep venous insufficiency," J. Cardiovasc. Pharmacol. Ther., Feb. 4, 2014.

Schmid-Schonbein, "Microlymphatics and lymph flow," Physiol Rev 70, 987-1028 (1990).

Shiba et al., "Human ES-cell-derived cardiomyocytes electrically couple and suppress arrhythmias in injured hearts," Nature 489, 332-335 (2012).

Shimizu et al., "Long-term survival and growth of pulsatile myocardial tissue grafts engineered by the layering of cardiomyocyte sheets," Tissue Eng. 12, 499-507 (2006a).

Shimizu et al., "Polysurgery of cell sheet grafts overcomes diffusion limits to produce thick, vascularized myocardial tissues," Faseb J. 20, 708-710 (2006b).

Sundaram et al., "Small diameter vascular graft engineered using human embryonic stem cell-derived mesenchymal cells," Tissue Eng. Part A (2013).

Takahashi et al., "Induction of pluripotent stem cells from mouse embryonic and adult fibroblast cultures by defined factors," Cell 126, 663-676 (2006).

Tambour et al., "Effect of physical therapy on breast cancer related lymphedema: protocol for a multicenter, randomized, single-blind, equivalence trial," BMC Cancer 14, 239 (2014).

Tandon et al., "Electrical stimulation systems for cardiac tissue engineering," Nat. Protoc. 4, 155-173 (2009).

Tandon et al., "Optimization of electrical stimulation parameters for cardiac tissue engineering," J. Tissue Eng. Regen. Med. 5, e115-25 (2011).

Thomas, "Managing venous stasis disease and ulcers," Clin. Geriatr. Med. 29, 415-424 (2013).

Thomson et al., "Proangiogenic microtemplated fibrin scaffolds containing aprotinin promote improved wound healing responses," Angiogenesis 17:195-205 (2014).

Williams et al., "A randomized controlled crossover study of manual lymphatic drainage therapy in women with breast cancer-related lymphoedema," Eur. J. Cancer Care (Engl). 11, 254-261 (2002).

Wolfson et al., "Pulsatile Venous Insufficiency in Severe Tricuspid Regurgitation: Does Pulsatility Protect Against Complications of Venous Disease?" Angiology 51, 231-239 (2000).

Xu et al., "Efficient generation and cryopreservation of cardiomyocytes derived from human embryonic stem cells," Regen. Med. 6, 53-66 (2011).

Yoshida et al., "In vitro tissue engineering of smooth muscle sheets with peristalsis using a murine induced pluripotent stem cell line," J. Pediatr. Surg. 47, 329-335 (2012).

Yuan et al., "Encapsulation of cardiomyocytes in a fibrin hydrogel for cardiac tissue engineering," J. Vis. Exp., 7 pages (2011).

Zervides et al., "Historical overview of venous valve prostheses for the treatment of deep venous valve insufficiency," J. Endovasc. Ther. 19, 281-290 (2012).

Zhu et al., "Neuregulin/ErbB signaling regulates cardiac subtype specification in differentiating human embryonic stem cells," Circ. Res. 107, 776-786 (2010).

Zhu et al., "Methods for the derivation and use of cardiomyocytes from human pluripotent stem cells," Methods Mol. Biol. 767, 419-431 (2011).

Zimmermann et al., "Tissue engineering of a differentiated cardiac muscle construct," Circ. Res. 90, 223-230 (2002).

* cited by examiner

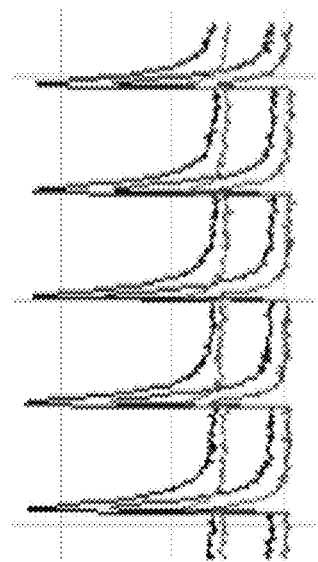
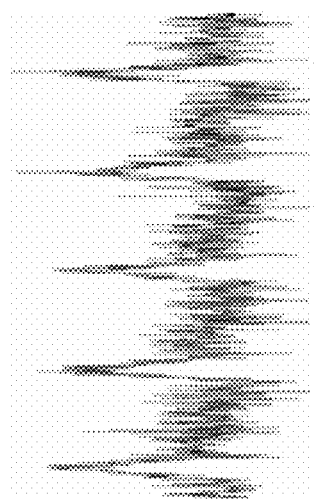
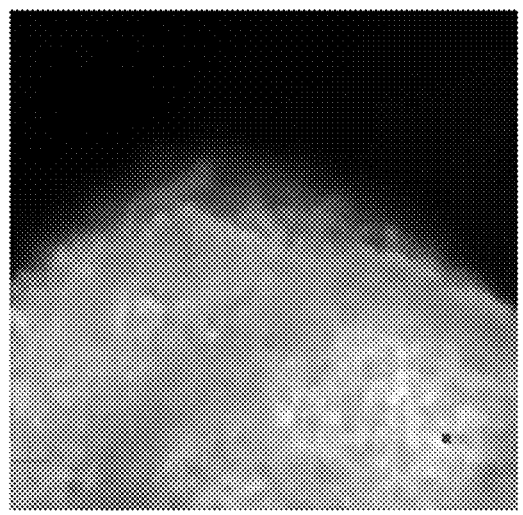
FIGS. 7A – 7B

MYOCYTE-DERIVED FLOW ASSIST DEVICE: EXTRAVASAL SHEATHS OF RHYTHMICALLY CONTRACTING MYOCYTES AIDING FLOW OF BIOLOGICAL FLUIDS

This is a continuation of U.S. application Ser. No. 14/889,830, filed Nov. 6, 2015, now allowed, which is a national stage application under 35 U.S.C. § 371 of PCT/US2014/038476 filed May 16, 2014, the entire contents of which are incorporated herein by reference and this application claims the benefit of the filing date of U.S. provisional application Ser. No. 61/824,180, filed May 16, 2013, and 61/905,491, filed Nov. 18, 2013, each of which is incorporated by reference herein in its entirety.

BACKGROUND INFORMATION

There are many biological fluids within our bodies. They include the aqueous humor of the eye, endolymph & perilymph contained within labyrinth of the inner ear, interstitial fluid, milk produced by mammary glands, amniotic fluid, chyme, chyle, gastric juices, lymph, seminal fluid, bile, cerebrospinal fluid and blood. There are a variety of conditions or diseases which result from impaired drainage or directional flow of such biological fluids, and which would benefit from a method to improve the drainage or directional flow. Among such conditions or diseases are, e.g., conditions related to impaired return of the blood to the heart (chronic venous insufficiency), and conditions resulting from impaired lymph flow, which are often referred to as lymphedema.

Chronic Venous Insufficiency

There are several auxiliary physiological mechanisms by which one's heart is assisted in its continuous effort to propel blood through vascular beds. There is the 'respiratory pump,' which acts via repetitive inflation/deflation cycles of the chest cavity that leads to a stretch of compliant veins leading to the heart. There is the so-called 'aortic pump' or Windkessel effect of the aorta, which helps to propel blood throughout the diastole as a result of elastic recoil. Finally, there is the 'skeletal muscle pump', which combats the effect of gravity in upright individuals. The skeletal muscle pump works via compression of nearby veins and requires functionally intact unidirectional valves within those veins.

When the skeletal muscle pump mechanism fails (either due to lack of skeletal muscle activity, distention of veins, failure of venous valves, or a combination of the above), it leads to chronic venous insufficiency, which is also called chronic venous disease (CVD). CVD is one of the most widespread diseases in the populations of the Western world. The number of people who suffer from CVD is very large, with an estimated 25% of adult population having varicose veins, and 6% more advanced chronic disease (Beebe-Dimmer et al., 2005). CVD can lead to chronic skin changes, phlebitis, venous stasis, ulceration and, ultimately, loss of a limb and death. Lower extremity ulcers are particularly common in diabetic patients, with venous disease accounting for majority of them (Greer et al., 2012). In United States alone, the annual cost associated with of CVD treatment is approaching $3 billion, constituting ~2% of the total healthcare budget cost (Robertson et al., 2008).

Today there are several treatments of CVD tailored to specific causes and symptoms. For varicose veins, there are non-surgical options such as sclerotherapy, leg elevation, and elastic stockings. These procedures can be helpful, but they require continuous care and are associated with lower quality of life. Surgical options include vein stripping, sealing veins using radiofrequency or laser energy, or ultrasound-guided foam sclerotherapy. These procedures can be effective, particularly when treating individual vein segments. Downsides of these treatments include high recurrence rate, often at a different site, and surgical complications. Venous leg ulcers are primarily treated using compression, with only 40% to 70% healing after 6 months of treatment (Thomas, 2013). Venous ulcers may get infected leading to cellulitis or gangrene and can eventually lead to amputation.

Impaired Lymph Flow or Lymphedema

The lymph system is a network of lymph vessels, tissues, and organs that carry lymph throughout the body. Lymphedema refers to an accumulation of interstitial fluid due to the insufficient capacity of the lymphatic system. Lymphedema may be inherited (primary) or caused by injury to the lymphatic vessels, in which case it is called secondary. Secondary lymphedema is one of the well-known complications of cancer treatment. It results from the dissection of lymph-nodes and subsequent radiation therapy. It is very commonly observed in breast cancer patients for whom the most common site of the disease is arm lymphedema (Didem et al., 2005). Lymphedema is also common in patients after surgical and radiation treatments of cervical and prostate cancers (Werngren-Elgström and Lidman, 1994). Depending on the surgical procedure, the type of the radiation therapy, and the techniques used to measure fluid accumulation, lymphedema incidence can range from 10 to 90% (Didem et al., 2005; Gärtner et al., 2009). When untreated, lymphedema becomes a chronic condition with the risk of worsening in terms of volume and degree of tissue fibrosis (Casley-Smith, 1995; Petrek et al., 2001). It can lead to cosmetic abnormalities, including limb discoloration and/or deformation. It also can impair patient's physical mobility, leading to mental discomfort and social isolation (Martín et al., 2011). Another adverse outcome can be an acute infection of the upper dermis and superficial lymphatics, caused by *streptococcus* bacteria. Today, the most common therapy consists of the following components; skin care, manual lymphatic drainage, bandaging and exercises (Brorson et al., 2008). Commonly used manual lymphatic drainage is time-consuming with no standardization among different physiotherapists (Tambour et al., 2014; Williams et al., 2002). Furthermore, the type of bandages used varies greatly. The scientific evidence as to what type of treatment or combination of treatments is most effective is scarce and/or controversial (Huang et al., 2013; Williams et al., 2002).

Even though very large numbers of people may be affected by chronic lymphedema, there is relatively little recognition of the seriousness of this chronic disease. However, it substantially increases postoperative medical costs for breast, prostate and cervical cancer survivors. In addition, up to 2/3 of obese individuals are thought to suffer from some aspects of lymphedema (Keast et al., 2014). As a result of improved cancer survival rates and the steadily growing number of overweight patients, the number of people who suffer from untreated or undertreated lymphedema has dramatically increased in recent years, particularly in Western societies. Yet, there is a limited arsenal of effective approaches to treat this debilitating condition. Patients' therapeutic options are few and new therapies to treat post-radiation lymphedema are critically needed.

There is a need for improved methods and devices to bring about improved drainage or directional flow of impaired venous blood or lymph.

DESCRIPTION OF THE DRAWINGS

(FIG. 1A) surrounding a vessel with a thick three dimensional construct of engineered muscle tissue (e.g. heart tissue); (FIG. 1B) wrapping a vessel with a plurality of prefabricated sheets of myocytes (e.g. cardiomyocytes) or thin layers of engineered muscle tissue (e.g. heart tissue); (FIG. 1C) wrapping a vessel with a prefabricated mesh of muscle fibers (e.g. cardiac fibers); (FIG. 1D) wrapping a vessel (e.g. a vein) with a single fiber wrapped in a spiral fashion.

(FIG. 2A) circumferential fiber layers; (FIG. 2B) one way helical arrangement; (FIG. 2C) two helixes wrapped in opposite directions; (FIG. 2D) a combination of circumferential and helical fiber orientation.

FIGS. 7A and 7B show spontaneously beating cardiac tissue constructs. (FIG. 7A) Flo-4 calcium indicator traces from four different regions of interests are shown to illustrate synchronous beating. (FIG. 7B) Spontaneously beating cardiac tissue constructs loaded with the voltage sensitive dye RH247. The trace shows regular electrical activity via optical action potential recordings.

FIG. 8B is a cartoon of two types of MFADs and an image of a culture dish with both types of MFAD as they appear on day 1, right after mixing scaffolds with the cells. After polymerization, cell culture media is added and dishes are placed in a cell culture incubator at 37 C, 95% Oxygen/5% $CO_2$.

(FIG. 10B) High magnification, revealing a homogeneous well-formed structure within connecting fibers; (FIG. 10C) an engineered muscle tissue fiber wrapped around an excised vein.

DESCRIPTION

Figures 1A, 1B, 1C, 1D:
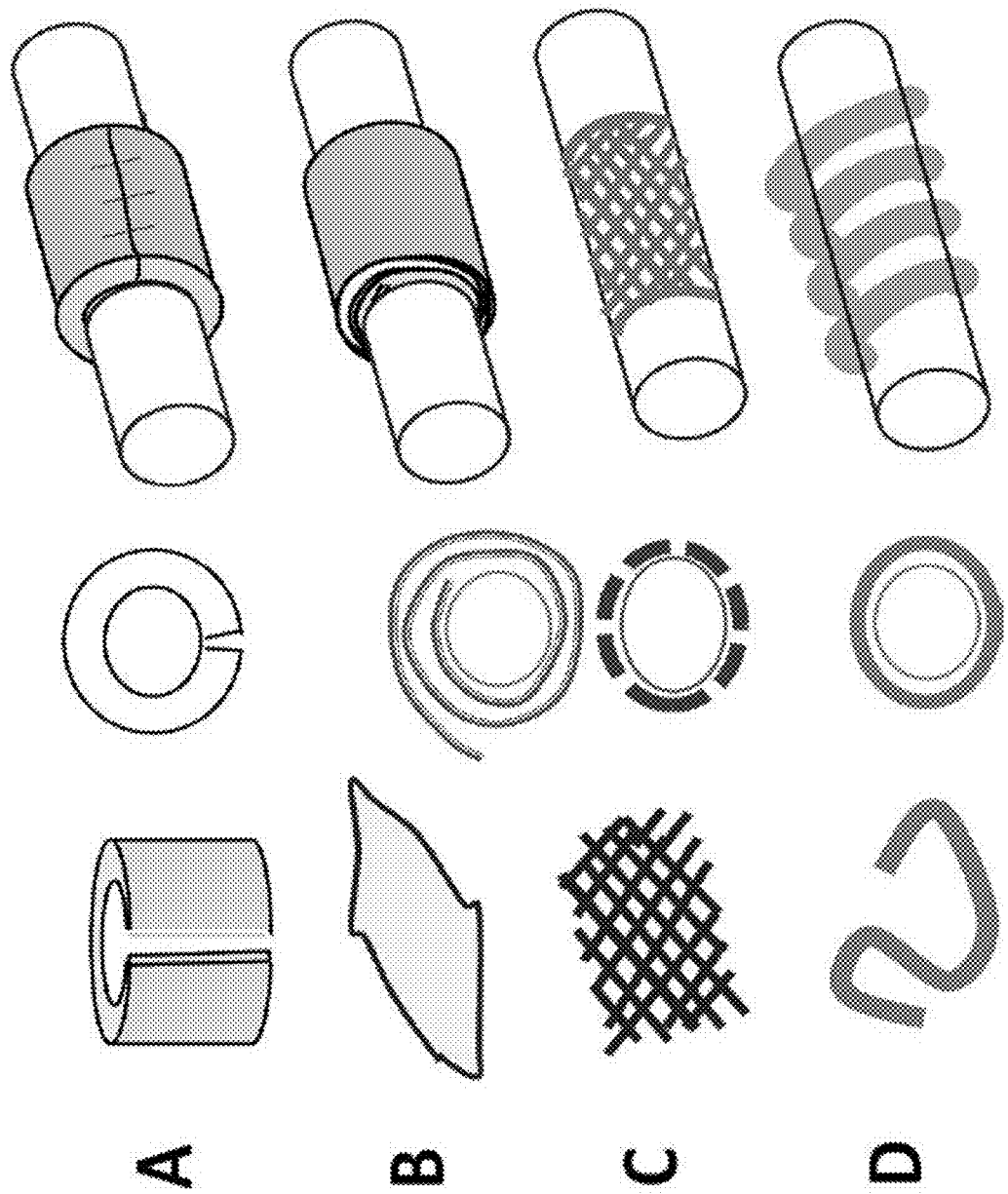
FIGS. 1A-1D show schematic drawings illustrating several types of MFAD designs, including.
Figures 2A, 2B, 2C, 2D:
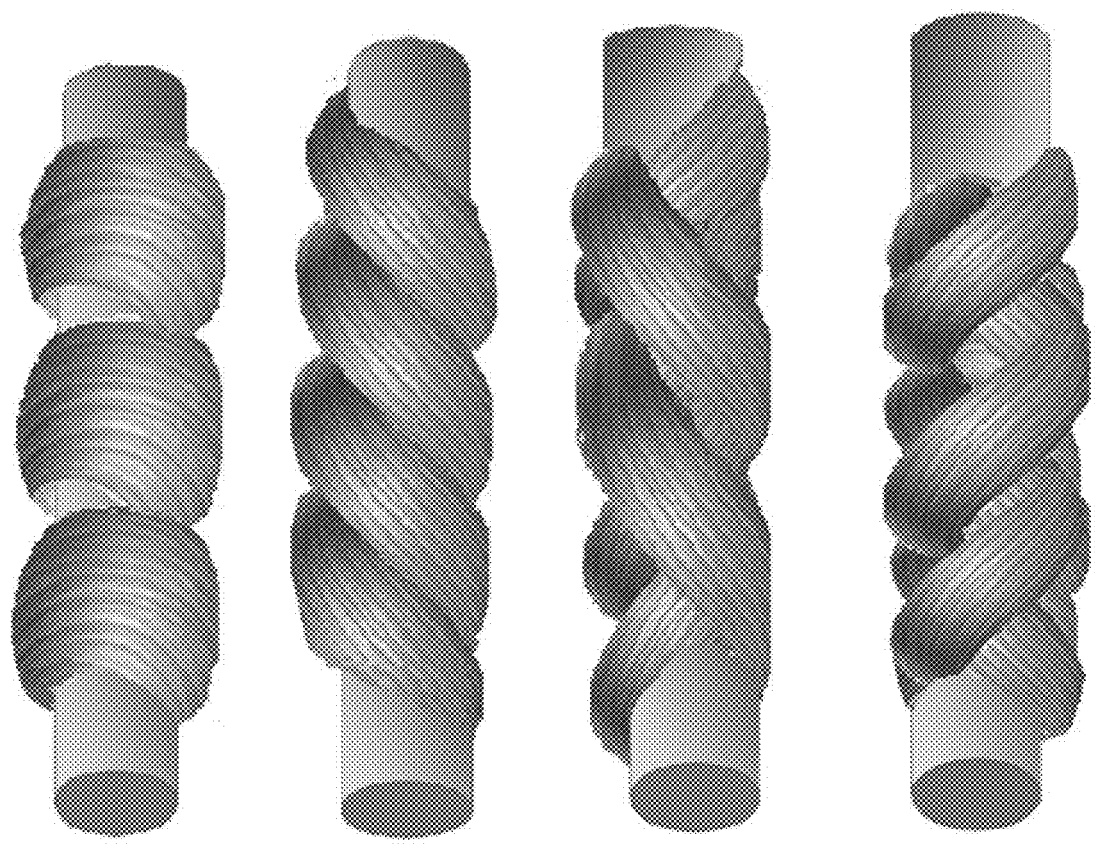
FIGS. 2A-2D are schematic drawings illustrating examples of ways of wrapping vessels with engineered muscle fiber.

This application relates, e.g., to a device and methods of using it to improve impaired (insufficient) drainage or directional flow of a biological fluid, including, for example, impaired return of blood to the heart (chronic venous insufficiency) or impaired lymph flow (lymphedema).

In one embodiment of the invention, stem cells, including induced pluripotent stem cells or another type of stem cell, are used to surround medium-sized vessels (about 1 mm to about 1 cm in diameter) in order to create a rhythmically beating sheath of muscle cells (myocytes). Such mini pumps resemble the simplest kinds of hearts seen in lower invertebrates and/or during human embryonic development. These primitive hearts are essentially muscular tubes which squeeze rhythmically moving fluid by peristaltic contraction. The placement of such a device around a vessel which exhibits impaired drainage or flow, such as a vein or a lymph vessel, leads to a significant improvement in the drainage or flow.

In general, the rhythmically beating cells which surround the vessel are myocytes or precursors thereof. These can be, e.g., smooth muscle cells or cardiomyocytes. The devices are sometimes referred to herein as Myocyte-based Flow Assist Devices (MFADs). In embodiments in which the cells are cardiomyocytes, the devices are sometimes referred to herein as Cardiomyocyte-based Venous Assist Devices (CMVADs). Although much of the discussion herein relates to cardiomyocyte-based MFADs, it is to be understood that the discussion also relates to MFADs in which the cells are smooth muscle cells.

One aspect of the invention is a myocyte-based flow assist device (MFAD) for treating a subject in need of increased flow of biological fluids, comprising a sheath which comprises rhythmically contracting myocytes. In one embodiment of the invention, the rhythmically contracting myocytes are immunologically compatible with the subject (e.g. are derived from the subject's own induced pluripotent stem cells).

In embodiments of the invention, the sheath further comprises a scaffold, within which are embedded the rhythmically contracting myocytes. The scaffold may be of biological origin (e.g. de-cellularized tissue slices, thrombin-fibrinogen based glues, silk, collagen, alginate, hyaluronic acid or any other biologically derived extra cellular matrix product), or it may be made of a chemical agent (e.g. a linkable synthetic polymer, such as, e.g., poly(lactic acid) (PLA), poly(lactide-co-glycolide) (PLGA), polyethylene glycol (PEG) or others).

The sheath may be in any of a variety of forms including, e.g., a) a (at least one, including many) thick sheet (e.g., having a combined thickness of about 0.2-5 mm); or b) a (at least one, including many) thin sheet (e.g., each individual sheet having a thickness of about 50-300 microns, providing a combined thickness of about 0.2-5 mm); or c) a mesh-like, woven, or prefabricated pattern of myocyte comprising fibers (which is formed, e.g., by using pre-fabricated pins or channels or by cutting matrix containing the cells during early stages of cultivation); or d) a coil-like arrangement of thick muscle fibers that results in a left-handed or right-handed helical arrangement or both. "Thick" muscle fibers, as used herein, refers to fibers having a diameter of about 0.2 mm to about 5 mm; or e) a combination of helical fiber arrangements with circumferential fiber alignment; or f) a combination of two or more the forms of MFAD of a)-e).

Some of these forms are shown schematically in FIGS. 1A-1D and FIGS. 2A-2D.

As used herein, the singular forms "a," "an," and "the" include plural referents unless the context clearly dictates otherwise. For example, in the preceding case, "a" thin sheet includes at least one, including many, thin sheets.

In one embodiment of the invention, the myocytes are cardiomyocytes. In another embodiment, the myocytes are smooth muscle cells.

In one embodiment of the invention, the sheath of an MFAD comprises a section that contains pacemaker-like cells while the rest of the sheath comprises ventricular-like cells. In one embodiment, both the section containing the pacemaker-like cells and the section containing the ventricular-like cells have a thickness of about 0.2-5 mm. The pacemaker-like section may be in a form of a ring which abuts the section comprising the ventricular-like cells; or it may be a distal portion of a fiber (e.g. a muscle fiber) that is coiled around the vessel.

In one embodiment, the MFAD comprises two thick rings, each having a thickness of about 0.2-5 mm, wherein the two thick rings are spatially separated; the first thick ring comprises pacemaker-like cells; and the second thick ring comprises ventricular-like cells; and wherein the MFAD further comprises a connecting section of cells (e.g. ventricular-like cells) which electrically couples the first and second thick rings.

The MFAD described above may further comprise one or more additional thick rings comprising ventricular-like cells, wherein the rings comprising ventricular-like cells are electrically coupled to each other with a connecting section that comprises conductive cells. These conductive cells can be ventricular-like cells, or other cells that can conduct the electrical signal from the pacemaker-like cells to the ventricular-like cells.

In any of the forms of MFAD described above, the sheath may comprise myocytes (e.g. cardiomyocytes or smooth muscle cells), having a thickness of about 50-300 microns, comprising a mixture of ventricular-like cells and pacemaker-like cells. For example, the MFAD may comprise two or more spatially separated rings of thin sheets, each comprising a mixture of ventricular-like cells and pacemaker-like cells.

In embodiments of the invention, the ventricular-like cells and the pacemaker-like cells have been differentiated from myocyte (e.g. cardiomyocyte or smooth muscle myocyte) precursor cells (including, e.g., induced pluripotent stem cells (iPS), embryonic stem cells (ESC), hematopoietic stem cells (HSC), or adipose stromal cells).

Another aspect of the invention is a method for making an MFAD of the invention, comprising a) placing a scaffold around a vessel to be treated, and injecting ventricular-like and/or pacemaker-like cells into suitable positions in the scaffold (e.g. (i) as a mixture of ventricular-like and pacemaker-like cells, or (ii) with the pacemaker-like cells positioned separately from the ventricular-like cells and at one end of the scaffold, upstream of the intended fluid flow); or b) seeding cardiomyocyte precursor cells onto, or embedding them into, a scaffold; culturing the scaffold comprising the cardiomyocyte precursor cells in vitro under suitable conditions to stimulate differentiation of the cardiomyocyte precursor cells into ventricular-like cells and/or pacemaker-like cells; or c) seeding, cells or their precursors onto, or embedding them into, a scaffold. When smooth muscle cells are used, adequate numbers of cells for use in an MFAD of the invention can be obtained directly from a subject, such as from a biopsy, scraping of a vein such as a varicose vein, auxiliary arteries, etc. They can also be generated from stem cell precursors (Cheung et al., 2014). The excised (harvested) cells can be seeded onto, or embedded into, a scaffold and cultured in vitro to increase the cell number and to introduce the cells into or onto a scaffold. The resulting smooth muscle cells generally exhibit a variety of spontaneously beating frequencies of contraction.

Smooth muscle cells spontaneously exhibit contractions and can serve as endogenous oscillators. Examples of such smooth muscle cell contraction include, e.g., waves of wall muscle contraction responsible for transporting esophageal and gut contents. Also, lymph propulsion is achieved by the spontaneous, rhythmic contractions of the surrounding smooth muscle layer which serves as an essential pump mechanism to propel lymph uphill against a hydrostatic pressure gradient from peripheral lymphatics through lymph nodes into the thoracic duct (Hargens and Zweifach, 1977; Schmid-Schonbein, 1990).

However, if desired, rhythmic activation can be provided by suitable cells, such as interstitial cells of Cajal, in a manner and in a relative orientation similar to the use of cardiac pacemaker cells to activate the beating of cardiac contractile cells (Nakatsu et al., 2013; Sakaguchi et al., 2013; Sundaram et al., 2013; Yoshida et al., 2012).

Another aspect of the invention is a method for treating a subject in need of increased peripheral venous blood flow, comprising implanting into the subject (surrounding a vein to be treated with) a MFAD of the invention; or a method for treating a subject in need of increased peripheral lymph flow, comprising implanting into the subject (surrounding a lymphatic vessel to be treated with) a MFAD of the invention. In this method, (a) the vessel to be treated may comprise one or more poorly functional unidirectional valves and/or does not comprise a unidirectional valve; and the method comprises implanting a scaffold which comprises ventricular-like cells and, located separately from the ventricular-like cells and at one end of the scaffold, pacemaker-like cells, which are positioned downstream of the intended blood flow direction, or (b) the vessel to be treated may comprise a unidirectional valve; and the method comprises implanting a MFAD which comprises a mixture of ventricular-like cells and pacemaker-like cells. In embodiments of this method, the method may further comprise, before implanting the MFAD, subjecting it to stretching, electrical stimulation, or culturing with a small piece of excised vessel, in order to improve mechanical performance of the MFAD; or it may be implanted in conjunction with a prosthetic vessel or a de-cellularized vessel.

A device or method of the invention can be used to treat any of a variety of conditions and diseases, including those mentioned elsewhere herein, as well as to improve performance of ageing but otherwise healthy organs. The ailments include, e.g., chronic deep venous disease and other causes of impaired peripheral blood flow, including direct muscle injury of lower limbs and/or skeletal muscle paralysis. As noted elsewhere herein, another large group of conditions and diseases is related to the compromised flow of lymphatic fluid leading to lymphedema. These conditions or diseases can be treated with a device or method of the invention.

Cells used in a device or method of the invention can be prepared by any of a variety of conventional methods. For example:

Pluripotent stem cells can be produced from a subject's own fibroblasts and/or other cell sources (Takahashi and Yamanaka, 2006). Optimization of these protocols allows one to produce large numbers of cells (Lundy et al., 2013; Xu et al., 2011). The use of iPS largely alleviates immunogenicity concerns. A skilled worker will recognize that other reprogrammable cell sources can also be used to generate myocytes with minimal immunogenicity (see, e.g., (Karabekian et al., 2011; Riolobos et al., 2013)). In some embodiments of the invention, the cells in an MFAD are immunologically compatible with the subject into which they are implanted.

One can selectively direct pluripotent stem cells (e.g., ESC or iPS cells) toward either pacemaker (or pacemaker-like), working ventricular (or ventricular-like) or atrial (atrial-like) cardiomyocyte phenotypes (Chow et al., 2013; Zhu et al., 2011). As used herein, the terms "pacemaker-like" and "ventricular-like" cells refer to cells that are developing toward their full pacemaker and contractile phenotypes (the latter phenotypes are well-known and characterized, e.g., for cells constituting the adult heart). Although immature cardiomyocytes may not be fully developed pacemaker, atrial or ventricular cells, they are sufficiently differentiated to function in the context of an MFAD. A skilled worker will recognize that although the "pacemaker-like" cells in the discussion above relate to cardiomyocytes, comparable pacemaker-like cells, such as for example interstitial cells of Cajal, can also be used to activate contractions for smooth muscle cells. "Ventricular-like" cells in the case of smooth muscle cells refers to smooth muscle cells which exhibit slow spontaneous beating frequency.

Protocols to derive smooth muscle cells from a variety of stem cell sources, including a subject's own cells, can be used (Cheung et al., 2014; Hosoyama et al., 2014; Sundaram et al., 2013). In contrast to cardiac myocytes, smooth muscle cells can be simply isolated from small pieces of a subject's own tissues, followed by in vitro proliferation to produce sufficient number of cells to make an MFAD.

Any of a variety of conventional biocompatible scaffolds can be used in order to create tissue constructs of the invention which are amenable to surgical manipulation.

Overall Design of MFADs

Some of the following discussion is directed to MFAD made of cardiomyocytes (CMVADs) and their use to enhance venous blood flow. However, a skilled worker will recognize how the methods can be adapted for designing and using MFADs comprising smooth muscle cells and/or for methods of enhancing lymph flow.

Figure 4:
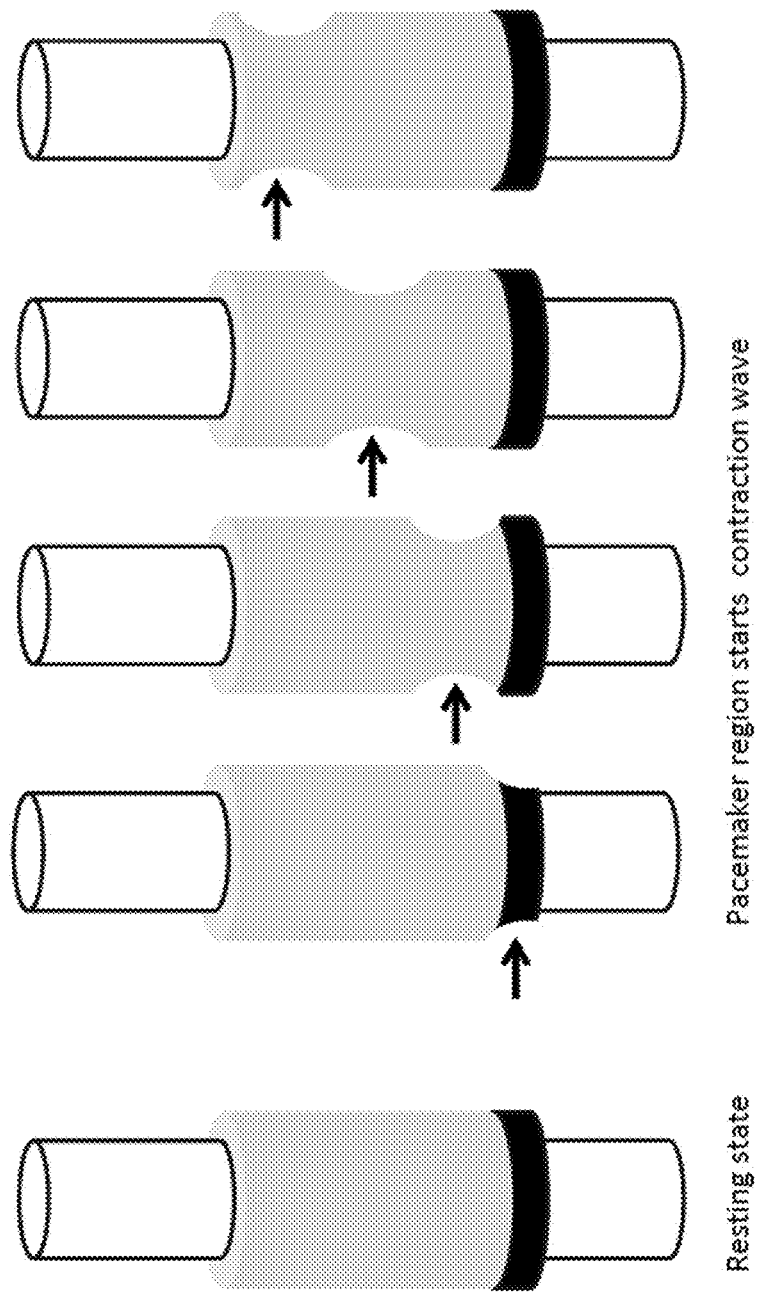
FIG. 4 shows a cartoon illustrating a propagating wave of contraction in a construct with a pacemaker ring. One can modulate the velocity of a propagating wave by changing the cell seeding density or by mixing cardiomyocytes with fibroblasts. For example, a higher ratio of fibroblasts to cardiomyocytes leads to a lower velocity.
Figures 5A, 5B, 5C, 5D:
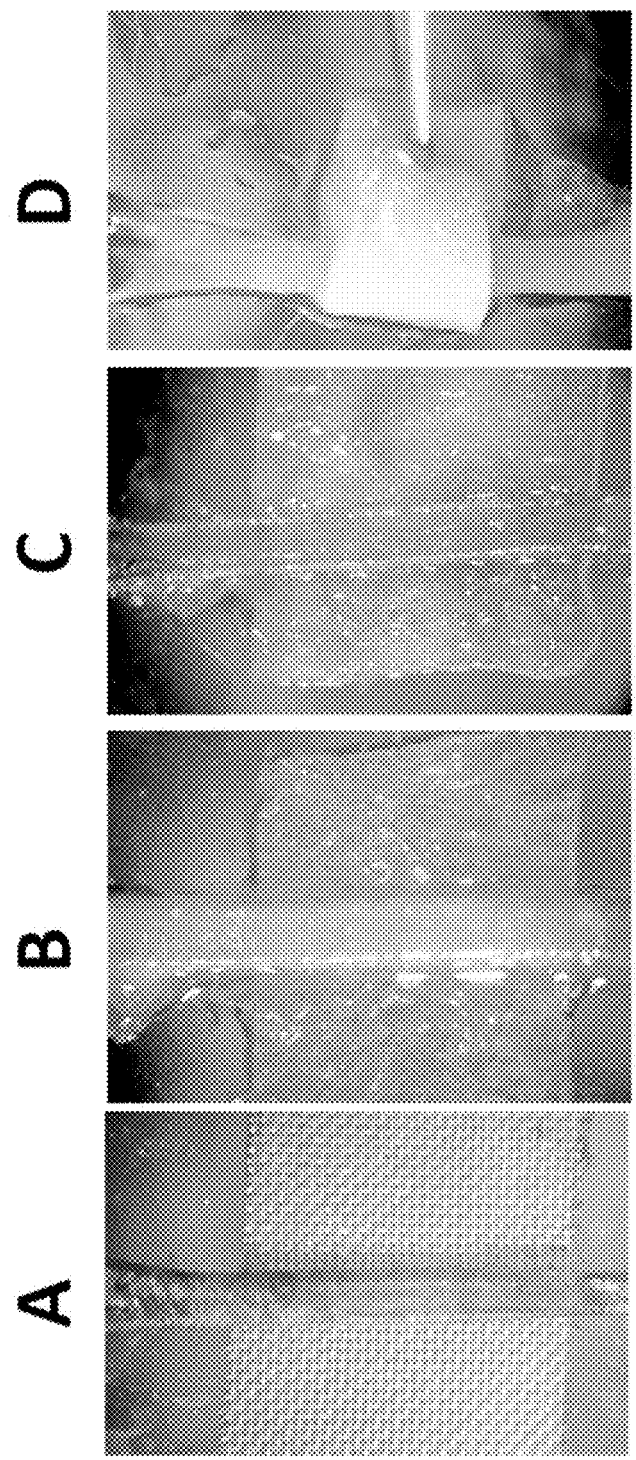
FIGS. 5A-5D show an excised rat iliac vein with three different scaffolds (FIG. 5A, FIG. 5B, FIG. 5C) and a scaffold wrapping step (FIG. 5D). They include artificial mesh (FIG. 5A), and thin (FIG. 5B) and thick (FIG. 5C) biopolymer meshes.

In general, two general types of MFADs (e.g. CMVADs) can be used. The first designs can be implanted around vessels that have a partially competent valve while the orifice of the valve has been distended creating reflux (FIG. 1A). In these cases, the cell content of an MFAD can be a simple mixture of pacemaker and ventricular cells. As the construct matures, these cells form gap junctions with each other creating an early form of syncytium (e.g., cardiac syncytium). As a result, the muscle sheath (or multiple muscle rings) contracts simultaneously while the unidirectional valve within the vessel enables unidirectional flow. The intrinsic beating rate of these MFADs can be altered by mixing in different ratios and combinations of nodal (i.e., pacemaker-like) and ventricular-like cells (e.g. ventricular cardiomyocytes). For example, increasing the ratio of pacemaker-like cells to ventricular-like cells will increase the beating rate. The second general type of MFAD design is used around vessels without functional or with severely damaged valves (FIG. 1B). This type of MFAD requires initial separation of pacemaker and ventricular like cells to create a device that squeezes the vessel in a peristaltic-like fashion. This can be done by creating an area with pacemaker cells upstream of intended blood flow direction. As the electrical wave of activity spreads from the pacemaker cell region to the rest of the construct, it creates a propagating wave of contraction (FIG. 4). By mixing in different ratios of ventricular-like cells (e.g. ventricular cardiomyocytes) and fibroblasts into an MFAD scaffold, one can modulate the propagation velocity and therefore MFAD propulsion force.

There are at least four general ways to create MFADs. They are illustrated in FIGS. 1A-1D and 2A-2D and include:
  A. surrounding a vessel by a three dimensional construct of engineered muscle tissue
  B. wrapping a vessel in prefabricated layers of engineered muscle tissue
  C. wrapping a vessel with a prefabricated mesh of muscle fibers.
  D. surrounding a vessel with coils of muscle fibers In one embodiment, the above designs are generated by first implanting bioscaffolds and then injecting myocyte precursors, or by first culturing bioscaffolds together with cardiomyocytes and then implanting them. Muscle fibers can be produced by any of a variety of procedures (See, e.g., (Bakunts et al., 2008; Bian et al., 2012; Khademhosseini et al., 2007; Nunes et al., 2013; Yuan Ye et al., 2011; Zimmermann et al., 2002). Similar methods can be used for generating and implanting smooth muscle cell based MFADs.

In some embodiments of the invention, the original scaffold may not be present in a MFAD which is implanted into a subject. For example, during the formation of an MFAD, myocyte precursors can be seeded onto a biodegradable scaffold, such as a fibrin scaffold. The biodegradable scaffold is degraded and slowly replaced by the extracellular matrix released by the cells. Other types of glue or extracellular matrix proteins can be used to hold the cells together until they connect and form their own matrix/scaffold.

Figures 3A, 3B, 3C, 3D, 3E:
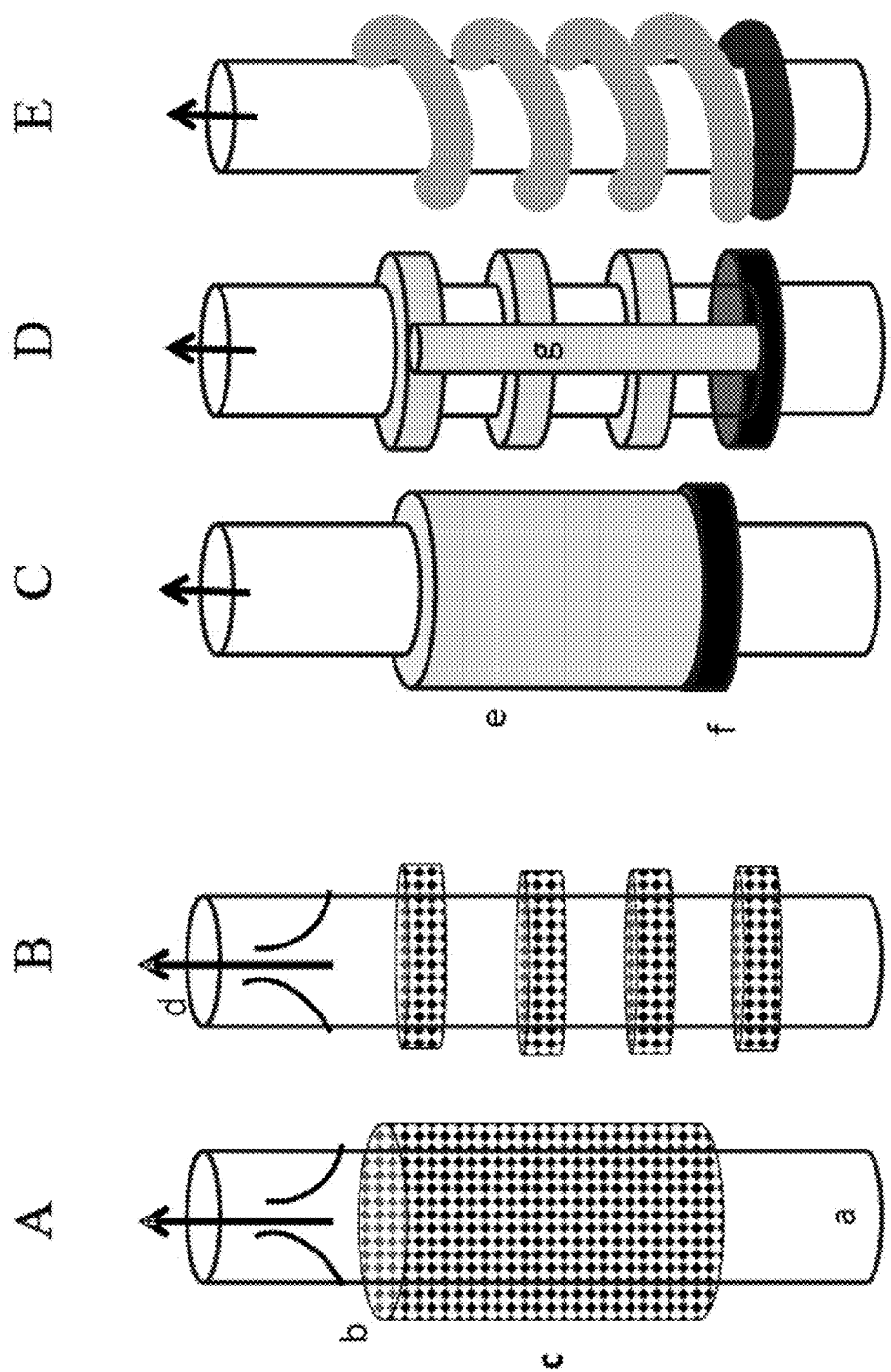
FIGS. 3A-3E are cartoons illustrating the placement of single (FIG. 3A), multiple (FIG. 3B), and pacemaker-layer driven MFADs (FIG. 3C, FIG. 3D), and coil-like (FIG. 3E) arrangements. a is a blood vessel; b is a unidirectional valve; c is an extravasal MFAD sheath made of a mixture of pacemaker & contractile cells; d shows arrows which indicate the direction of blood flow; e shows a long MFAD made of coupled contractile cells; f shows pacemaker cell rich layer (or an area); g shows a layer of conductive tissue connecting individual short MFADs to create a peristaltic effect.

FIGS. 3A-3E show a basic MFAD (FIG. 3A), multiple MFADs (FIG. 3B), an MFAD with a spatially separate pacemaker region (FIG. 3C) and coupled rings of MFAD with a pacemaker ring (FIG. 3D). The MFAD designs such as shown in FIGS. 3A and 3B can be implanted around vessel sites that have unidirectional valves. In these cases, the cell content of the MFAD can be a mixture of pacemaker and ventricular cells. As a result, the MFAD sheath (or multiple MFAD rings) contracts simultaneously while a unidirectional valve within the vessel will allows unidirectional flow. The MFAD design shown in FIGS. 3C and 3D employs a separation of the pacemaker-like and ventricular-like cells. This type of design can be used in vessels with poorly functional or absent unidirectional valves. When MFAD scaffolds are seeded with pacemaker cells upstream of the intended blood flow direction, it creates a propagating wave of contraction. It then squeezes the vessel moving flow in a peristaltic fashion (FIG. 4).

Rings or sections of cells can be "coupled" electrically with, e.g., a connecting section (member) which electrically couples the rings or sections. For example, myocytes form connections to each other via gap junctions. This makes them electrically coupled and the wave of contraction can then occur. Connecting segments in MFADs can be made of myocytes (e.g. pacemakers or pacemaker-like cells, such as between two rings comprising ventricular-like cells; or ventricular-like cells, such as between a first ring comprising ventricular-like cells and a second ring comprising pacemaker-like cells).

Composition of MFAD Scaffolds.

Scaffolds into which myocyte precursors are seeded can be of biological or chemical origin. The first group can include, e.g., de-cellularized tissue slices, thrombin-fibrinogen based glues or sheets made of other biologically derived extracellular matrix proteins, which will be evident to a skilled worker (see, e.g., FIGS. 5A-5D). The second group includes any of a variety of conventional linkable polymers that can create highly controllable scaffolds with different degree of architectural complexity. A variety of types of such linkable polymers will be evident to a skilled worker. (See, e.g., (Ahmed et al., 2012, 2008; Carletti et al., 2011; Madden et al., 2010; Thomson et al., 2013).

MFAD Cell Sources.

Figures 6A, 6B:
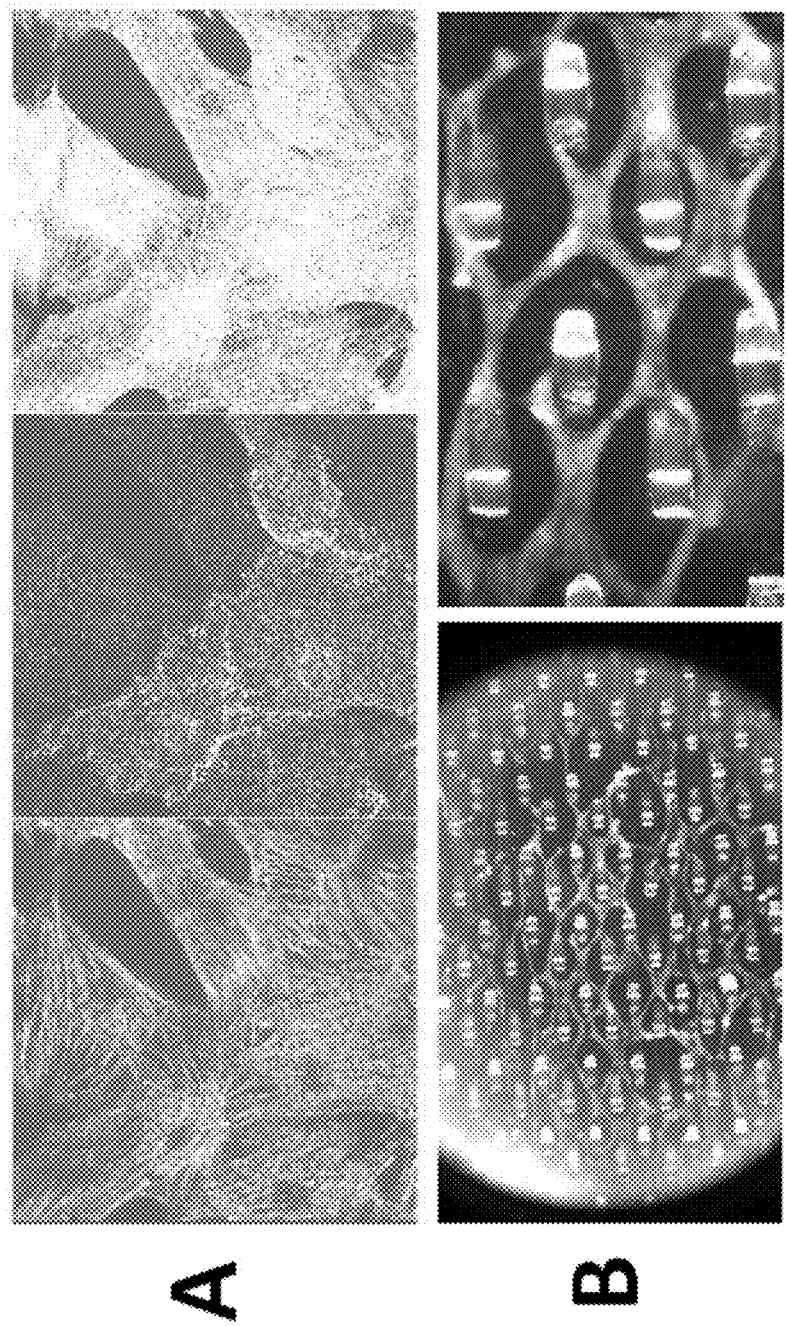
FIGS. 6A and 6B show (FIG. 6A) immunostaining of embryonic stem cell-derived cardiomyocytes for cardiac markers (anti-actinin—left panel), connexin 43 (middle panel) and DAPI (right panel) and (FIG. 6B) low and high magnification images of cardiac fibers. These were created by plating immature cardiomyocytes mixed with 10% matrigel onto a regular arrangement of pins.

A variety of cell sources can be used to create an MFAD. One choice is a subject's own iPS that can be derived from fibroblasts. Alternatively, a number of other stem cell like sources give rise to functional cardiomyocytes, including hemopoetic cells, cells from fat tissues, ESC cell lines and others progenitors (FIG. 6A). This list continues to grow, so the ultimate source of cardiomyocyte precursors to seed future MFADs depends on a combination of ethical, medical and financial factors.

A variety of methods will be evident to a skilled worker for selectively directing pluripotent stem cells (e.g., ESC or iPS cells) toward either a pacemaker or working ventricular cell phenotype. See, e.g., (Zhu et al., 2010). In some embodiments of the invention, agents are introduced into the cells in order to turn on specific genes that allow selections of cells with a particular lineage or phenotype. In other embodiments, the cells are genetically modified by siRNA or with self-excisable vectors which insert antibiotic resistance genes etc. that are linked to a specific promoter. When under antibiotic pressure, cells (pre-treated with different vectors) will then exhibit survival advantage based on their selective phenotype.

Such differentiated pacemaker-like or ventricular-like cells can be injected separately into suitable scaffolds surrounding a vessel to be treated. In another embodiment, two rings, one comprising pacemaker and one comprising ventricular cells are cultured separately, then connected into one structure. As the cells grow and mature, the cells in the two rings will connect to each other.

In some embodiments of the invention, a mixture of pacemaker and ventricular cell types is desirable. Unless special protocols like the ones described above are employed, myocyte precursors generally differentiate into spontaneously beating cells with mixed phenotypes. Therefore, such immature cells can be used to form rings or other components of MFAD that comprise a mixture of these cell types. Alternatively, a mixture of more mature nodal and ventricular cells can be mixed together.

Both the pacemaker and ventricular phenotypes, either individually or as a mixture of the two, can be used to create functional venous assist devices as described herein.

Culturing of Seeded Scaffolds

When myocyte precursors are combined with the scaffold of choice and then cultured using standard cell culture conditions—as either cell sheets, fiber networks (FIG. 6B) or small pieces of tissue (FIG. 6)—they form spontaneously contracting muscle tissue. Calcium indicators (FIG. 7A) or voltage sensitive dyes (FIG. 7B) reveal synchronous calcium transients and action potential recordings across different regions of these construct.

Figure 8A:
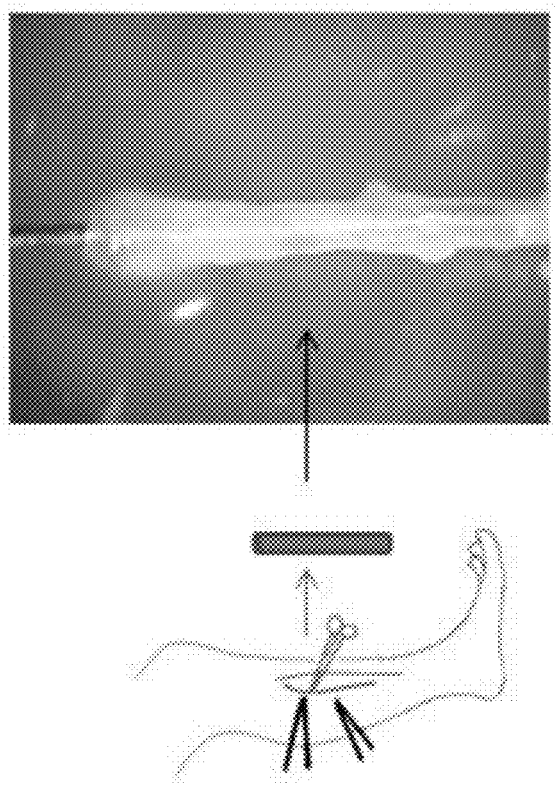
FIGS. 8A and 8B are cartoons illustrating vein segment excision, followed by an image of excised rat iliac vein with a needle inside.
Figure 8B:
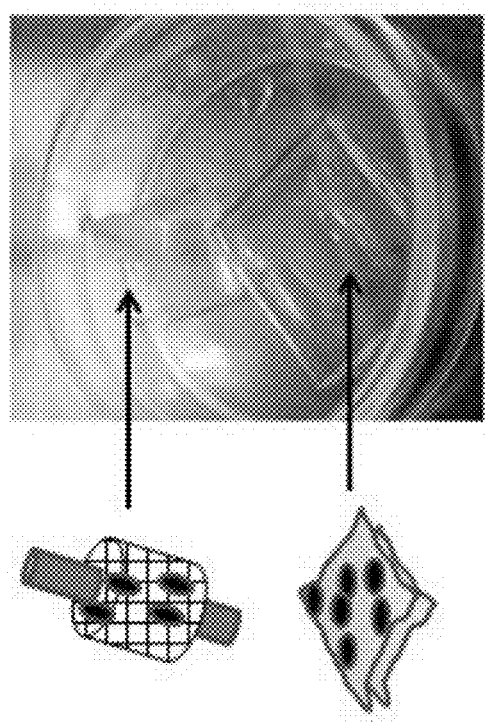

When engineered muscle tissue constructs are electrically and mechanically stimulated, cell alignment and cardiomyocyte maturation are improved, leading to a better mechanical performance (Tandon et al., 2009, 2011). Therefore, additional ex-vivo procedures, such as stretching and electrical stimulation, can be used to improve force development and quality of MFAD before their implantation. MFAD can be also cultured together with a small piece of excised vessel (FIGS. 8A and 8B). In the latter case, the vessel itself can act as a stretchable balloon upon connecting it to a pulsatile pressure source.

Implantation of MFADs

Figure 9:
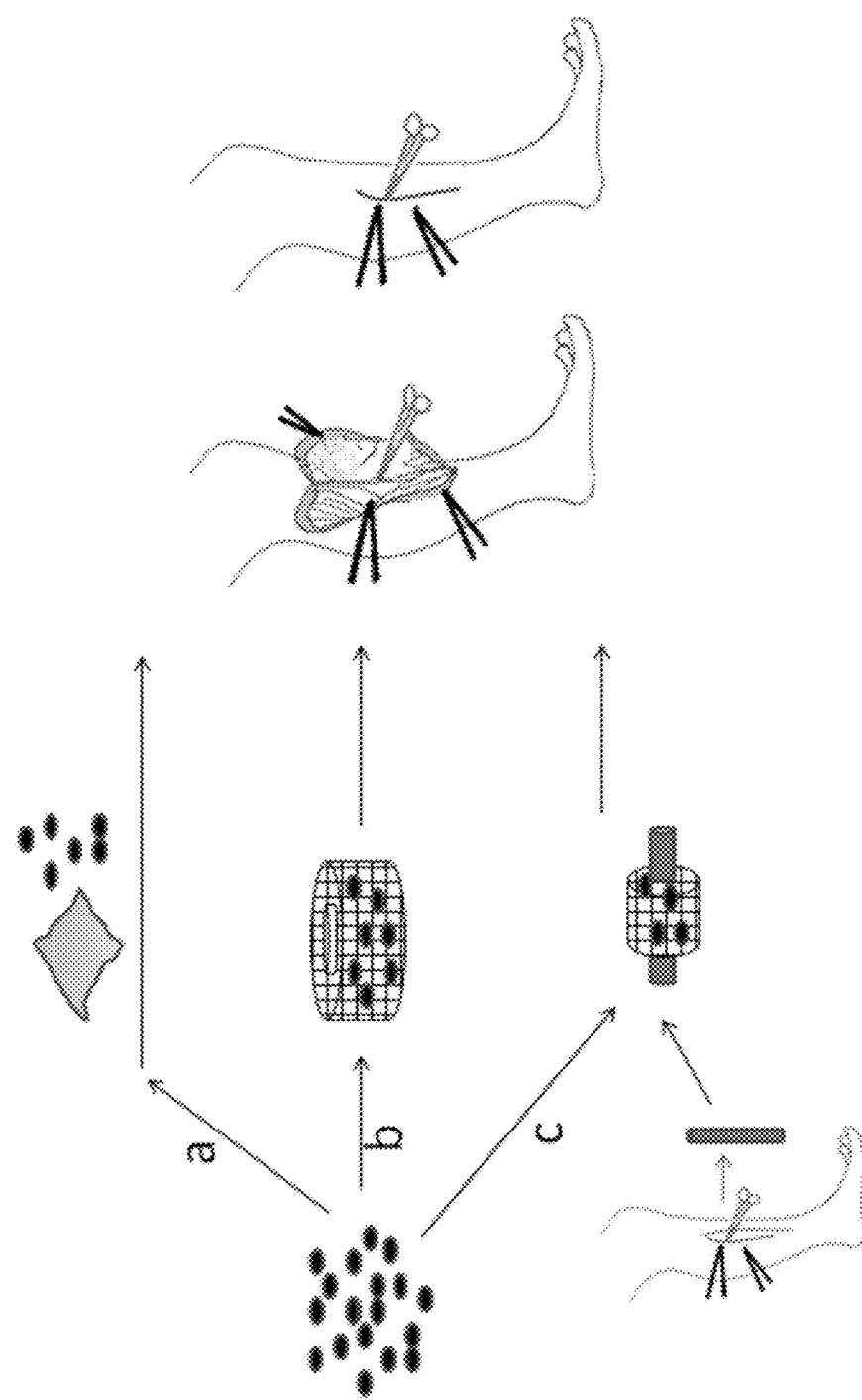
FIG. 9 is a cartoon illustrating different scenarios of MFADs implantation. The process starts with myocyte precursors (iPS-CM, ESC-CM, tissue SC, etc) that are seeded onto a) a scaffold which is pre-placed around the affected vein; b) an in vitro scaffold, followed by culturing, electrical stimulation and/or mechanical stretch; c) a scaffold that is placed around an excised vein. All three scenarios are followed by either open flap or laparoscopic surgery to implant the MFADs.
Figures 10A, 10B, 10C:
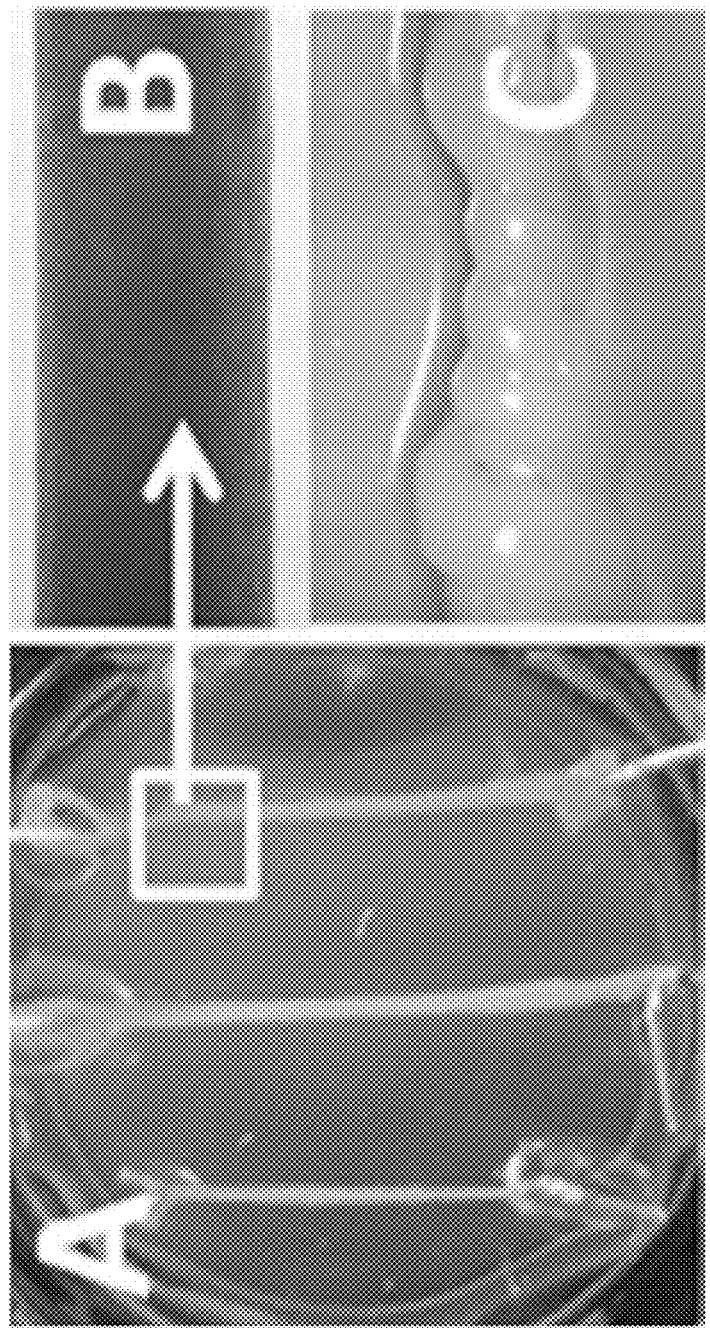
FIGS. 10A-10C show (FIG. 10A) Preformed collagen engineered muscle tissue fibers pinned to a plastic mold in a 3 cm culture dish.
Figures 11A, 11B, 11C:
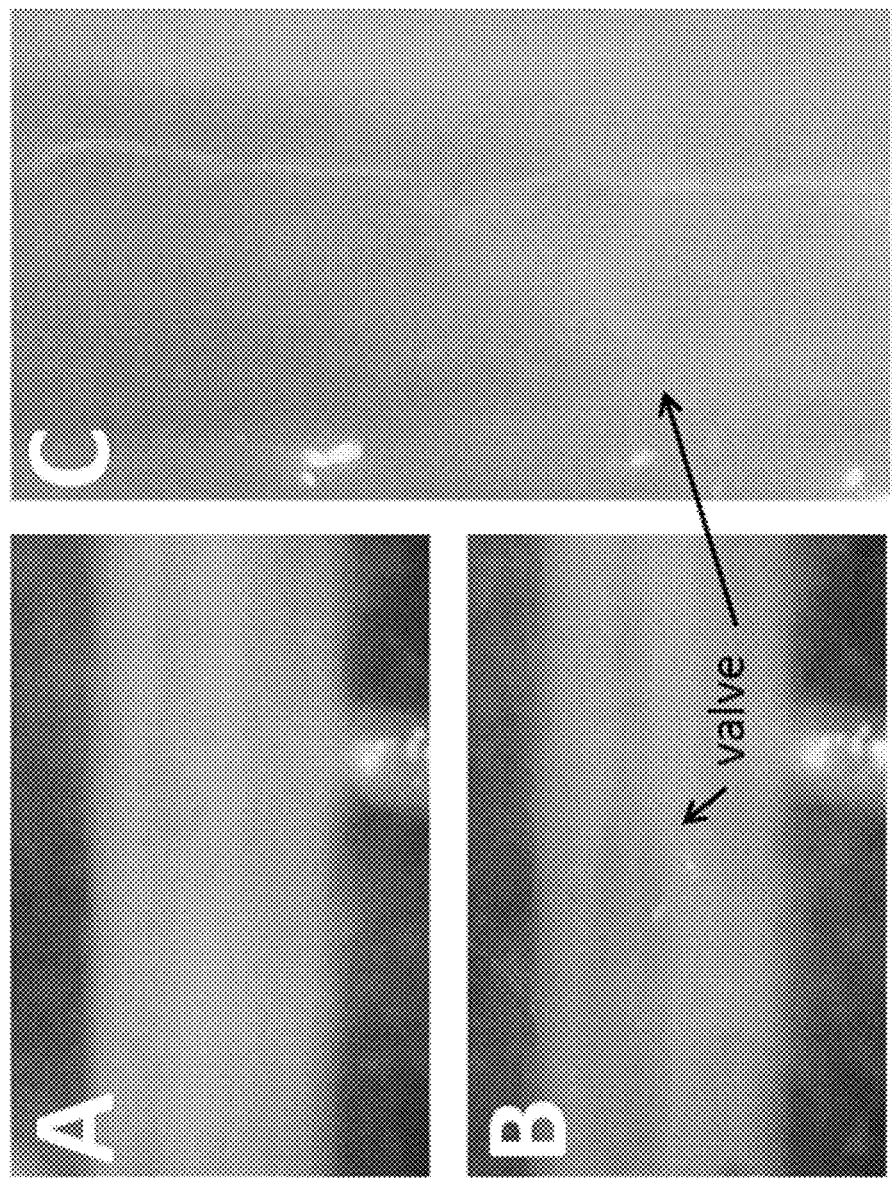
FIGS. 11A-11C show an excised segment of a rabbit posterior tibial vein containing a valve. The latter can be located by 'milking' the vein which empties the vein (FIG. 11A), followed by its refill (FIG. 11B). Bulging valvular sinus and valve cusps can then be clearly seen (FIG. 11C).
Figure 12:
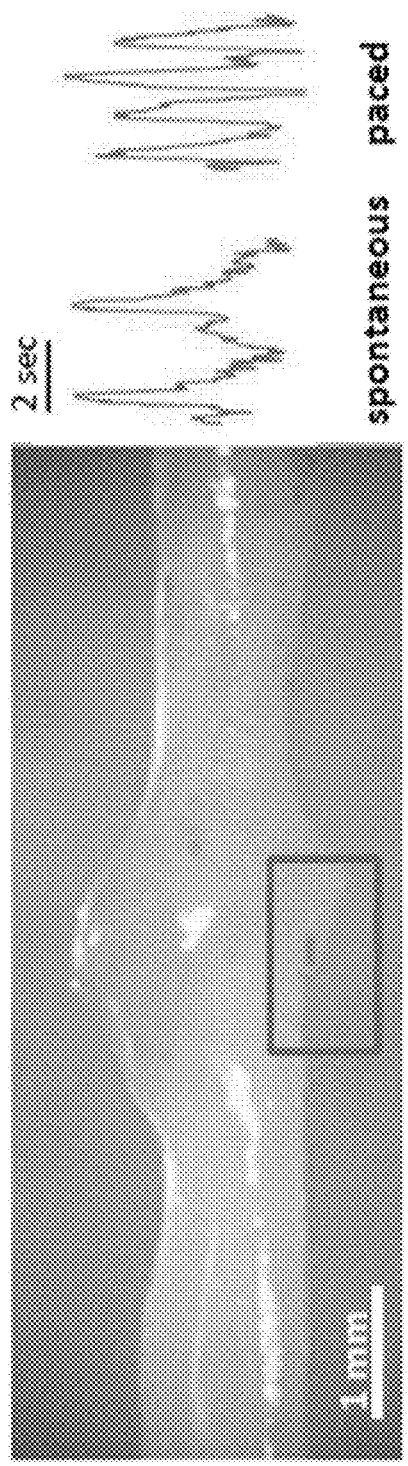
FIG. 12 shows a beating MFAD made using an excised segment of a rabbit posterior tibial vein. Motion traces acquired from a region of interest shown by the grey rectangle are depicted on the right. The MFAD contracts spontaneously and can also be paced at desired frequencies.

The final step of the process is the implantation of an MFAD around a vessel (e.g. vein or lymph vessel) of interest. Three different scenarios to create and implant an MFAD are shown in FIG. 9. In all cases, one starts with myocyte precursors, followed by their seeding into scaffold and then implantation. In scenario (a) a scaffold is implanted first, followed by cell injection. In scenario (b) a cell-seeded scaffold is first cultured, then implanted into patient. In scenario (c), a vessel segment is first excised from a subject, followed by creation of an MFAD around it, and then re-implanted into the patient. Instead of excising a patient's vessel, one can also use prosthetic vessels or decellularized vessels from allogeneic or xenogeneic sources. After creating an MFAD, one can use the newly formed self-pumping vessel to either replace or bypass a poorly functioning one.

Any of a variety of subjects can be treated with an MFAD of the invention. A "subject" can be any subject (patient) that exhibits impaired drainage or directional flow of a biological fluid, such a venous blood or lymph, and that would benefit from a method to improve the drainage or directional flow. Suitable subjects include, e.g., mammals, including laboratory animals, such as mice, rats, rabbits, guinea pigs and non-human primates; pets, such as dogs and cats; farm animals, such as cows and sheep; sporting animals, such as horses; and humans.

MFADs of the invention exhibit advantages over other methods for regenerating the functional capacity of organs, such as heart, with stem cell-based therapies. The following discussion is directed primarily to cardiomyocyte based MFADs (CMVADs) used to enhance venous blood flow. However, the considerations described herein also apply to MFADs in which the contractile cells are smooth muscle cells and/or to methods of enhancing lymph flow.

Contractile Force.

One of the major hurdles of cardiac tissue engineering is the need to create a muscle which is strong and thick enough to create pressures of 100-150 mmHg, or greater. This is not a trivial task and has led many to doubt that tissue engineered heart can be achieved (Eschenhagen and Zimmermann, 2005). By contrast, MFADs do not need to be very powerful in order to work. This is because the pressure needed on the venous side is about order of magnitude lower than one on the arterial side, i.e., about 10 mmHg vs about 100 mmHg. Secondly, because the typical diameter of a medium sized vein (about 1 cm) is much smaller than the ventricular cavity (~10 cm), the Law of LaPlace predicts that proportionally less wall tension is needed to create the same transmural pressure. Together, these two factors indicate that only a fraction of a contractile force of native cardiac muscle is sufficient to produce pulsatile compression of a vein by an MFAD.

Viability & Nutrient Supply.

As noted above, a MFAD sheath does not need to be very thick. This eliminates a second major concern of cardiac engineering, i.e. the need to vascularize tissues which are over 300 micron thick. Being thin and in close proximity to the main blood vessel, an MFAD will survive initial grafting without problems. Eventually, small vessels grow into the MFAD providing additional flow and nutrients.

Macroscopic Tissue Architecture.

Another concern of cardiac tissue engineering is how to re-create an anatomically and functionally complex heart on both macroscopic (multiple chambers, sinoatrial and atrioventricular nodes, valves, nerves) and microscopic (orientation of myocytes, fibroblasts, capillaries, extracellular matrix, etc.) levels. These concerns are not applicable to MFADs, since they are designed to function as a primitive, tube-like heart. As such they can be made from a simple mixture of immature cardiomyocytes of any origin, and a full maturation of these cells is not required.

Graft-Induced Arrhythmias.

Another major concern of cardiac regeneration is that potential arrhythmias may be caused by the endogenous pacemaker activity of the grafts (Shiba et al., 2012). However, since MFADs are not implanted into the heart, cardiac arrhythmias are not a concern.

Tumor Formation.

The cardiomyocyte based MFADs are made from terminally differentiated cells, so their ability to cause cancer should be comparable to that of other cells in the body. The proliferation of stem cell derived cardiomyocytes rapidly tapers off (Laflamme et al., 2005), minimizing concerns that MFADs will expand and impinge on the vessel lumen.

Skeletal Muscle Twitches.

In the unlikely event that a rhythmically beating Snit causes unwanted twitches of surrounding skeletal muscle, a layer of collagen or other protective material can be placed around an MFAD to prevent the coupling of cardiomyocyte to skeletal muscle.

Thrombogenesis

MFADs are positioned outside of a vessel, so the endothelial lining of the veins is not impacted, minimizing any concerns of thrombus formation, fibroblast proliferation and/or wound-repair related valve changes or closures.

Number of MFADs

Studies with valvular reconstruction or transplantation of excised autologous valves have shown that replacement of even a single valve can lead to significant improvements in an affected limb (Maleti and Perrin, 2011; Pavcnik et al., 2007; Zervides and Giannoukas, 2012). These studies support our findings that a finite number of MFADs can make a significant difference in a patient's outcome.

Extravasal Stenting

In addition to its pumping mechanism, extravasal MFADs provide a structural support to a distended vein, acting as an external stent that can help to bring valve cusps together.

Self Adjustable Pump

Cardiomyocyte based MFADs are intrinsically myogenic, i.e., upon more stretch, the contraction is stronger. This occurs due to the Frank-Starling mechanism. The latter is based on stretch dependent increase in myofilament calcium sensitivity and increased number of cross-bridges. This mechanism has been shown to be fully operational in engineered cardiac tissue constructs (Eschenhagen et al., 2002). As a result, MFADs act as self-adjustable pumps. In a standing position which increases hydrostatic pressure, MFADs are stretched, leading to an increased force of contraction. Once pressure is relieved and/or a patient lies down, the strength of MFADs pumping action automatically decreases.

Pulsatile Flow

Even if MFADs are not strong enough to fully combat hydrostatic pressure upon standing, their rhythmic contraction leads to pressure pulsations within the vein. Such pulsatile shear stress enhances secretion of cytokines by venous endothelial cells and, consequently, counteracts a predisposition to platelet aggregation, hypercoagulability, and white cell adhesion, diminishing thrombosis and promoting healing of leg ulcers (Wolfson et al., 2000)

Long-Term Effects on the Cardiovascular System

By placing cardiac cells outside the heart to help venous return from lower extremities, one can prevent edema, ultimately helping flow throughout the entire circulatory system, including heart muscle itself. Subjects with failing hearts can be treated with their small, strategically placed MFAD counterparts—not only around veins of lower extremities with impaired valves, but around other essential blood vessels.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited herein, including U.S. provisional application Ser. No. 61/824,180, filed May 16, 2013, and 61/905,491, filed Nov. 18, 2013, and in the figures are hereby incorporated in their entirety by reference, particularly with regard to the information for which they are cited.

REFERENCES

Ahmed, M., Yildirimer, L., Khademhosseini, A., and Seifalian, A. M. (2012). Nanostructured materials for cardiovascular tissue engineering. J. Nanosci. Nanotechnol. 12, 4775-4785.

Ahmed, T. A. E., Dare, E. V, and Hincke, M. (2008). Fibrin: a versatile scaffold for tissue engineering applications. Tissue Eng. Part B Rev. 14, 199-215.

Bakunts, K., Gillum, N., Karabekian, Z., and Sarvazyan, N. (2008). Formation of cardiac fibers in Matrigel matrix. Biotechniques 44, 341-348.

Beebe-Dimmer, J. L., Pfeifer, J. R., Engle, J. S., and Schottenfeld, D. (2005). The epidemiology of chronic venous insufficiency and varicose veins. Ann. Epidemiol. 15, 175-184.

Bian, W., Juhas, M., Pfeiler, T. W., and Bursac, N. (2012). Local tissue geometry determines contractile force generation of engineered muscle networks. Tissue Eng. Part A 18, 957-967.

Brorson, H., Ohlin, K., Olsson, G., Svensson, B., and Svensson, H. (2008). Controlled compression and liposuction treatment for lower extremity lymphedema. Lymphology 41, 52-63.

Carletti, E., Motta, A., and Migliaresi, C. (2011). Scaffolds for tissue engineering and 3D cell culture. Methods Mol. Biol. 695, 17-39.

Casley-Smith, J. R. (1995). Alterations of untreated lymphedema and it's grades over time. Lymphology 28, 174-185.

Cheung, C., Bernardo, A. S., Pedersen, R. A., and Sinha, S. (2014). Directed differentiation of embryonic origin-specific vascular smooth muscle subtypes from human pluripotent stem cells. Nat. Protoc. 9, 929-938.

Chow, M. Z. Y., Geng, L., Kong, C.-W., Keung, W., Fung, J. C.-K., Boheler, K. R., and Li, R. A. (2013). Epigenetic regulation of the electrophysiological phenotype of human embryonic stem cell-derived ventricular cardiomyocytes: insights for driven maturation and hypertrophic growth. Stem Cells Dev. 22, 2678-2690.

Dai, W., Hale, S. L., and Kloner, R. A. (2004). Implantation of immature neonatal cardiac cells into the wall of the aorta in rats: a novel model for studying morphological and functional development of heart cells in an extracardiac environment. Circulation 110, 324-329.

Dai, W., Hale, S. L., and Kloner, R. A. (2006). Cardiac cells implanted within the outer aortic wall of rats generate measurable contractile force. Regen. Med. 1, 119-124.

Dai, W., Hale, S. L., and Kloner, R. A. (2007). Development of a spontaneously beating vein by cardiomyocyte transplantation in the wall of the inferior vena cava in a rat: A pilot study. J. Vasc. Surg. 45, 817-820.

Didem, K., Ufuk, Y. S., Serdar, S., and Zümre, A. (2005). The comparison of two different physiotherapy methods in treatment of lymphedema after breast surgery. Breast Cancer Res. Treat. 93, 49-54.

Dongaonkar, R. M., Quick, C. M., Vo, J. C., Meisner, J. K., Laine, G. A., Davis, M. J., and Stewart, R. H. (2012). Blood flow augmentation by intrinsic venular contraction in vivo. Am. J. Physiol. Regul. Integr. Comp. Physiol. 302, R1436-42.

Eschenhagen, T., and Zimmermann, W. H. (2005). Engineering myocardial tissue. Circ. Res. 97, 1220-1231.

Eschenhagen, T., Didié, M., Heubach, J., Ravens, U., and Zimmermann, W.-H. (2002). Cardiac tissue engineering. Transpl. Immunol. 9, 315-321.

Gärtner, R., Jensen, M.-B., Nielsen, J., Ewertz, M., Kroman, N., and Kehlet, H. (2009). Prevalence of and factors associated with persistent pain following breast cancer surgery. JAMA 302, 1985-1992.

Greer, N., Foman, N., Dorrian, J., Fitzgerald, P., MacDonald, R., Rutks, I., and Wilt, T. (2012). Advanced Wound Care Therapies for Non-Healing Diabetic, Venous, and Arterial Ulcers: A Systematic Review.

Hargens, A. R., and Zweifach, B. W. (1977). Contractile stimuli in collecting lymph vessels. Am J Physiol Hear. Circ Physiol 233, H57-65.

Hosoyama, T., McGivern, J. V, Van Dyke, J. M., Ebert, A. D., and Suzuki, M. (2014). Derivation of myogenic progenitors directly from human pluripotent stem cells using a sphere-based culture. Stem Cells Transl. Med. 3, 564-574.

Huang, T.-W., Tseng, S.-H., Lin, C.-C., Bai, C.-H., Chen, C.-S., Hung, C.-S., Wu, C.-H., and Tam, K.-W. (2013). Effects of manual lymphatic drainage on breast cancer-related lymphedema:

a systematic review and meta-analysis of randomized controlled trials. World J. Surg. Oncol. 11, 15.

Joh, J.-H., Lee, K.-B., Yun, W.-S., Lee, B.-B., Kim, Y.-W., and Kim, D.-I. (2009). External banding valvuloplasty for incompetence of the great saphenous vein: 10-year results. Int. J. Angiol. 18, 25-28.

Karabekian, Z., Posnack, N. G., and Sarvazyan, N. (2011) Immunological Barriers to Stem-Cell Based Cardiac Repair. Stem Cell Rev. 7, 315-325.

Keast, D. H., Despatis, M., Allen, J. O., and Brassard, A. (2014). Chronic oedema/lymphoedema: under-recognised and under-treated. Int. Wound J.

Khademhosseini, A., Eng, G., Yeh, J., Kucharczyk, P. A., Langer, R., Vunjak-Novakovic, G., and Radisic, M. (2007). Microfluidic patterning for fabrication of contractile cardiac organoids. Biomed. Microdevices 9, 149-157.

Laflamme, M. A., Gold, J., Xu, C., Hassanipour, M., Rosier, E., Police, S., Muskheli, V., and Murry, C. E. (2005). Formation of Human Myocardium in the Rat Heart from Human Embryonic Stem Cells. Am. J. Pathol. 167, 663-671.

Lundy, S. D., Zhu, W.-Z., Regnier, M., and Laflamme, M. (2013). Structural and Functional Maturation of Cardiomyocytes Derived From Human Pluripotent Stem Cells. Stem Cells Dev.

Lurie, F., Kistner, R., Perrin, M., Raju, S., Neglen, P., and Maleti, 0. (2010). Invasive treatment of deep venous disease. A UIP consensus. Int. Angiol. 29, 199-204.

Madden, L. R., Mortisen, D. J., Sussman, E. M., Dupras, S. K., Fugate, J. A., Cuy, J. L., Hauch, K. D., Laflamme, M. A., Murry, C. E., and Ratner, B. D. (2010). Proangiogenic scaffolds as functional templates for cardiac tissue engineering. Proc. Natl. Acad. Sci. U.S.A 107, 15211-15216.

Maleti, O., and Perrin, M. (2011). Reconstructive surgery for deep vein reflux in the lower limbs: techniques, results and indications. Eur. J. Vasc. Endovasc. Surg. 41, 837-848.

Martín, M. L., Hernández, M. A., Avendaño, C., Rodríguez, F., and Martínez, H. (2011). Manual lymphatic drainage therapy in patients with breast cancer related lymphoedema. BMC Cancer 11, 94.

Meissner, M. H., Moneta, G., Burnand, K., Gloviczki, P., Lohr, J. M., Lurie, F., Mattos, M. A., McLafferty, R. B., Mozes, G., Rutherford, R. B., et al. (2007). The hemodynamics and diagnosis of venous disease. J. Vasc. Surg. 46 Suppl S, 4S-24S.

Nakatsu, H., Ueno, T., Oga, A., Nakao, M., Nishimura, T., Kobayashi, S., and Oka, M. (2013). Influence of mesenchymal stem cells on stomach tissue engineering using small intestinal submucosa. J. Tissue Eng. Regen. Med.

Nunes, S. S., Miklas, J. W., Liu, J., Aschar-Sobbi, R., Xiao, Y., Zhang, B., Jiang, J., Massé, S., Gagliardi, M., Hsieh, A., et al. (2013). Biowire: a platform for maturation of human pluripotent stem cell-derived cardiomyocytes. Nat. Methods 10, 781-787.

Opie, J. C., Izdebski, T., Payne, D. N., and Opie, S. R. (2008). Monocusp—novel common femoral vein monocusp surgery uncorrectable chronic venous insufficiency with aplastic/dysplastic valves. Phlebology 23, 158-171.

Pavcnik, D., Yin, Q., Uchida, B., Park, W. K., Hoppe, H., Kim, M. D., Keller, F. S., and Rösch, J. (2007). Percutaneous autologous venous valve transplantation: short-term feasibility study in an ovine model. J. Vasc. Surg. 46, 338-345.

Petrek, J. A., Senie, R. T., Peters, M., and Rosen, P. P. (2001). Lymphedema in a cohort of breast carcinoma survivors 20 years after diagnosis. Cancer 92, 1368-1377.

Phillips, M. N., Dijkstra, M. L., Khin, N. Y., and Lane, R. J. (2013). Endovenous valve transfer for chronic deep venous insufficiency. Eur. J. Vasc. Endovasc. Surg. 46, 360-365.

Riolobos, L., Hirata, R. K., Turtle, C. J., Wang, P.-R., Gornalusse, G. G., Zavajlevski, M., Riddell, S. R., and Russell, D. W. (2013). HLA engineering of human pluripotent stem cells. Mol. Ther. 21, 1232-1241.

Robertson, L., Evans, C., and Fowkes, F. G. R. (2008). Epidemiology of chronic venous disease. Phlebology 23, 103-111.

Sakaguchi, K., Shimizu, T., Horaguchi, S., Sekine, H., Yamato, M., Umezu, M., and Okano, T. (2013). In vitro engineering of vascularized tissue surrogates. Sci. Rep. 3, 1316.

Sarvazyan, N. (2014). Thinking outside the heart: Use of engineered cardiac tissue for treatment of chronic deep venous insufficiency. J. Cardiovasc. Pharmacol. Ther. February 4.

Schmid-Schonbein, G. W. (1990). Microlymphatics and lymph flow. Physiol Rev 70, 987-1028.

Shiba, Y., Fernandes, S., Zhu, W.-Z., Filice, D., Muskheli, V., Kim, J, Palpant, N. J., Gantz, J., Moyes, K. W., Reinecke, H., et al. (2012). Human ES-cell-derived cardiomyocytes electrically couple and suppress arrhythmias in injured hearts. Nature 489, 332-335.

Shimizu, T., Sekine, H., Isoi, Y., Yamato, M., Kikuchi, A., and Okano, T. (2006a). Long-term survival and growth of pulsatile myocardial tissue grafts engineered by the layering of cardiomyocyte sheets. Tissue Eng. 12, 499-507.

Shimizu, T., Sekine, H., Yang, J., Isoi, Y., Yamato, M., Kikuchi, A., Kobayashi, E., and Okano, T. (2006b). Polysurgery of cell sheet grafts overcomes diffusion limits to produce thick, vascularized myocardial tissues. FASEB J. 20, 708-710.

Sundaram, S., Echter, A., Sivarapatna, A., Qiu, C., and Niklason, L. (2013). Small diameter vascular graft engineered using human embryonic stem cell-derived mesenchymal cells. Tissue Eng. Part A.

Takahashi, K., and Yamanaka, S. (2006). Induction of pluripotent stem cells from mouse embryonic and adult fibroblast cultures by defined factors. Cell 126, 663-676.

Tambour, M., Tange, B., Christensen, R., and Gram, B. (2014). Effect of physical therapy on breast cancer related lymphedema: protocol for a multicenter, randomized, single-blind, equivalence trial. BMC Cancer 14, 239.

Tandon, N., Cannizzaro, C., Chao, P.-H. G., Maidhof, R., Marsano, A., Au, H. T. H., Radisic, M., and Vunjak-Novakovic, G. (2009). Electrical stimulation systems for cardiac tissue engineering. Nat. Protoc. 4, 155-173.

Tandon, N., Marsano, A., Maidhof, R., Wan, L., Park, H., and Vunjak-Novakovic, G. (2011). Optimization of electrical stimulation parameters for cardiac tissue engineering. J. Tissue Eng. Regen. Med. 5, e115-25.

Thomas, D. R. (2013). Managing venous stasis disease and ulcers. Clin. Geriatr. Med. 29, 415-424.

Thomson, K. S., Dupras, S. K., Murry, C. E., Scatena, M., and Regnier, M. (2013). Proangiogenic microtemplated fibrin scaffolds containing aprotinin promote improved wound healing responses. Angiogenesis.

Werngren-Elgström, M., and Lidman, D. (1994). Lymphoedema of the lower extremities after surgery and radiotherapy for cancer of the cervix. Scand. J. Plast. Reconstr. Surg. Hand Surg. 28, 289-293.

Williams, A. F., Vadgama, A., Franks, P. J., and Mortimer, P. S. (2002). A randomized controlled crossover study of manual lymphatic drainage therapy in women with breast cancer-related lymphoedema. Eur. J. Cancer Care (Engl). 11, 254-261.

Wolfson, V., Tsikonova, I., Keren, D., Barmeir, E., Yeshurun, D., and Naschitz, J. E. (2000). Pulsatile Venous Insufficiency in Severe Tricuspid Regurgitation: Does Pulsatility Protect Against Complications of Venous Disease? Angiology 51, 231-239.

Xu, C., Police, S., Hassanipour, M., Li, Y., Chen, Y., Priest, C., O'Sullivan, C., Laflamme, M. A., Zhu, W.-Z., Van Biber, B., et al. (2011). Efficient generation and cryopreservation of cardiomyocytes derived from human embryonic stem cells. Regen. Med. 6, 53-66.

Yoshida, A., Chitcholtan, K., Evans, J. J., Nock, V., and Beasley, S. W. (2012). In vitro tissue engineering of smooth muscle sheets with peristalsis using a murine induced pluripotent stem cell line. J. Pediatr. Surg. 47, 329-335.

Yuan Ye, K., Sullivan, K. E., and Black, L. D. (2011). Encapsulation of cardiomyocytes in a fibrin hydrogel for cardiac tissue engineering. J. Vis. Exp.

Zervides, C., and Giannoukas, A. D. (2012). Historical overview of venous valve prostheses for the treatment of deep venous valve insufficiency. J. Endovasc. Ther. 19, 281-290.

Zhu, W.-Z., Xie, Y., Moyes, K. W., Gold, J. D., Askari, B., and Laflamme, M. A. (2010). Neuregulin/ErbB signaling regulates cardiac subtype specification in differentiating human embryonic stem cells. Circ. Res. 107, 776-786.

Zhu, W.-Z., Van Biber, B., and Laflamme, M. A. (2011). Methods for the derivation and use of cardiomyocytes from human pluripotent stem cells. Methods Mol. Biol. 767, 419-431.

Zimmermann, W.-H., Schneiderbanger, K., Schubert, P., Didié, M., Münzel, F., Heubach, J. F., Kostin, S., Neuhuber, W. L., and Eschenhagen, T. (2002). Tissue engineering of a differentiated cardiac muscle construct. Circ. Res. 90, 223-230.

What is claimed is:

1. A Myocyte-based Flow Assist Device (MFAD) for treating a subject in need of increased flow of biological fluids, comprising:
   a vessel segment; and
   a sheath which comprises rhythmically contracting myocytes, the sheath disposed on at least a portion of a surface of the vessel segment,
   wherein the sheath further comprises at least one sheet of myocytes formed into a ring, and
   wherein the sheath further comprises a scaffold, within which are embedded the rhythmically contracting myocytes.

2. The MFAD of claim 1, wherein the myocytes are immunologically compatible with the subject.

3. The MFAD of claim 1, wherein the scaffold is of biological origin.

4. The MFAD of claim 1, wherein the scaffold is made of a chemical agent.

5. The MFAD of claim 1, wherein the sheath is in the form of at least one of:

a thick sheet, having a thickness of about 0.2-5 mm; or one or more thin sheets, each individual sheet having a thickness of about 50-300 microns, providing a combined thickness of about 0.2-5 mm; or a mesh-like, woven, or prefabricated pattern of myocyte comprising fibers; or a coil-like arrangement of thick muscle fibers that results in a left-handed or right-handed helical arrangement or both; or a combination of helical fiber arrangements with circumferential fiber alignment.

6. The MFAD of claim 1, wherein the myocytes are cardiomyocytes.

7. The MFAD of claim 1, wherein the myocytes are smooth muscle cells.

8. A Myocyte-based Flow Assist Device (MFAD) for treating a subject in need of increased flow of biological fluids, comprising:
a vessel segment; and
a sheath which comprises rhythmically contracting myocytes, the sheath disposed on at least a portion of a surface of the vessel segment,
wherein the sheath further comprises at least one sheet of myocytes formed into a ring, and
wherein the sheath comprises a section that comprises peacemaker-like cells while the rest of the sheath comprises ventricular-like cells.

9. The MFAD of claim 8, wherein
the pacemaker-like section is in a form of a ring which abuts the section comprising the ventricular-like cells, or
the pacemaker-like section is a distal portion of a fiber that is coiled around the vessel segment.

10. The MFAD of claim 8, which comprises two thick rings, each having a thickness of about 0.2-5 mm, wherein the two thick rings are spatially separated; the first thick ring comprises pacemaker-like cells; and the second thick ring comprises ventricular-like cells; and
wherein the MFAD further comprises a connecting section of cells which electrically couples the first and second thick rings.

11. The MFAD of claim 10, which further contains one or more additional thick rings comprising ventricular-like cells, wherein the rings comprising ventricular-like cells are electrically coupled to each other with a connecting section that comprises conductive cells.

12. A Myocyte-based Flow Assist Device (MFAD) for treating a subject in need of increased flow of biological fluids, comprising:
a vessel segment; and
a sheath which comprises rhythmically contracting myocytes, the sheath disposed on at least a portion of a surface of the vessel segment,
wherein the sheath further comprises at least one sheet of myocytes formed into a ring, and
wherein the sheath comprises a thin sheet of myocytes, having a thickness of about 50-300 microns, comprising a mixture of ventricular-like cells and pacemaker-like cells.

13. The MFAD of claim 12, wherein the sheath comprises a plurality of spatially separated rings of thin sheets, each comprising a mixture of ventricular-like cells and pacemaker-like cells.

14. The MFAD of claim 12, wherein the ventricular-like cells and the pacemaker-like cells have been differentiated from myocyte precursor cells.

15. The MFAD of claim 1, wherein the vessel segment comprises a biological tissue excised from the subject, is a prosthetic vessel, or is a decellularized vessel.

* * * * *